United States Patent
Patel et al.

(10) Patent No.: US 11,400,203 B2
(45) Date of Patent: Aug. 2, 2022

(54) POST-OPERATIVE SURGICAL SITE WOUND TREATMENT AND METHOD FOR DEVICE REMOVAL

(71) Applicants: Cor Medical Ventures, Inc., Solana Beach, CA (US); The Regents of the University of Colorado, a body corporate, Denver, CO (US)

(72) Inventors: Vikas Patel, Denver, CO (US); Christopher Kleck, Englewood, CA (US); Brian Bowman, Carlsbad, CA (US); Tina John, San Diego, CA (US); Jude Paganelli, San Diego, CA (US)

(73) Assignees: Cor Medical Ventures, Inc., Del Mar, CA (US); The Regents of the University of Colorado, a body corporate, Denver, CO (US)

( * ) Notice: Subject to any disclaimer, the term of this patent is extended or adjusted under 35 U.S.C. 154(b) by 93 days.

(21) Appl. No.: 16/796,826

(22) Filed: Feb. 20, 2020

(65) Prior Publication Data
US 2020/0330660 A1    Oct. 22, 2020

Related U.S. Application Data

(63) Continuation of application No. PCT/US2018/047587, filed on Aug. 22, 2018.
(Continued)

(51) Int. Cl.
*A61M 1/00* (2006.01)
*A61F 13/02* (2006.01)
*A61F 13/00* (2006.01)

(52) U.S. Cl.
CPC .......... *A61M 1/90* (2021.05); *A61F 13/0216* (2013.01); *A61M 1/0058* (2013.01); *A61M 1/85* (2021.05); *A61F 2013/0054* (2013.01)

(58) Field of Classification Search
CPC .......... A61M 1/90; A61M 27/00; A61M 1/23; A61M 1/912; A61M 1/915;
(Continued)

(56) References Cited

U.S. PATENT DOCUMENTS

| 8,133,214 B2 | 3/2012 | Hayase et al. |
| 2004/0249360 A1 | 12/2004 | Spehalski |

(Continued)

FOREIGN PATENT DOCUMENTS

| AU | 2016202644 A1 | 5/2016 |
| WO | WO-2019040656 A1 | 2/2019 |

OTHER PUBLICATIONS

The extended European search report for Application No. EP 18848115.4, dated May 10, 2021, (6 pages).
(Continued)

*Primary Examiner* — Tatyana Zalukaeva
*Assistant Examiner* — Nhu Q. Tran
(74) *Attorney, Agent, or Firm* — Acuity IP, LLC; Nathan S. Cassell

(57) ABSTRACT

A device and method for treatment of post-operative surgical site wounds. Device includes an elongated hollow shaft that spans from the wound closure to the deep wound area, the internal end abutting a wound dressing and the external end connecting to a device that can provide negative-pressure suction and irrigation. Device providing one or more of irrigation, suction, and/or local antibiotic delivery to deep infections through a closed-wound. The method for removal includes narrowing a removal element relative to the long axis, collapsing the wound dressing; removing the wound dressing through the elongated shaft; and removing the device through a closed wound, avoiding a second removal surgery.

20 Claims, 29 Drawing Sheets

Related U.S. Application Data

(60) Provisional application No. 62/549,357, filed on Aug. 23, 2017.

(58) Field of Classification Search
CPC ............... A61F 13/00068; A61F 13/36; A61F 2013/0054; A61F 2013/00536
See application file for complete search history.

(56) References Cited

U.S. PATENT DOCUMENTS

| | | |
|---|---|---|
| 2013/0023840 A1 | 1/2013 | Loske et al. |
| 2013/0123723 A1 | 5/2013 | Tout et al. |
| 2015/0306287 A1 | 10/2015 | Burdick |
| 2016/0206369 A1 | 7/2016 | Frech et al. |

OTHER PUBLICATIONS

PCT/US2018/047587 Search Report & Written Opinion dated Oct. 17, 2018.

POST-OPERATIVE SURGICAL SITE WOUND TREATMENT AND METHOD FOR DEVICE REMOVAL

CROSS-REFERENCE

This application is a continuation application of International Application No. PCT/US2018/047587, filed Aug. 22, 2018, which claims the benefit of U.S. Provisional Application No. 62/549,357, filed Aug. 23, 2017, which application is incorporated herein by reference.

BACKGROUND OF THE INVENTION

Surgical drains are often used to treat deep post-operative wounds. Surgical drains are tubes commonly placed by surgeons to remove blood, pus, and infected fluids from a wound bed and to prevent the accumulation of air, or formation of dead space. If allowed to accumulate, the fluids or air can put pressure on the surgical site and adjacent areas, causing pain. There are several types of surgical drains including open or closed, and suction or passive drains. Closed-suction drains are maintained under low or high pressure to create a suction and drain into a bag or bottle.

The general surgical drain protocol involves inserting a drain into the wound and attaching the external end to a suction source. The negative pressure from the suction source removes exudates from the cavity. The wound can be closed around the drain. Surgical drains may fail to suction over the entire wound area and when removed, often still leave a relatively large dead space.

Negative-pressure wound therapy (NPWT) is used to promote healing in acute or chronic wounds. A sealed wound dressing fills the wound, attaching to a vacuum pump to apply reduced pressure, such as sub-atmospheric pressure. The vacuum acts as a suction device, removing fluid from the wound and drawing the edges of the wound inward. Additionally, sub-atmospheric pressure assists in wound closure by promoting blood flow to the area and stimulating granulation tissue formation. NPWT systems can also provide irrigation or antibiotics to the wound.

The general NPWT protocol involves placing the wound dressing in the wound and placing a flexible cover layer over the wound to create a seal, or vacuum reservoir, where the reduced pressure can be applied. The NPWT tubing can then be attached to the wound dressing at the skin level with an adhesive transfer pad.

NPWT systems can also be used for deep post-operative wound closure. The wound dressing is packed into the deep wound and is attached to a suction drainage system that can provide irrigation and remove exudates through the negative pressure system. The wound can be closed temporarily but a removal surgery is necessary to remove the dressing from the wound, leaving a relatively large dead space.

Therefore, there is a need for improved surgical site wound management devices, systems and methods that overcome some of the challenges associated with commercially available technology. The present disclosure describes improvements over existing technologies to allow for more complete post-operative surgical site wound management.

SUMMARY OF THE INVENTION

The present disclosure generally relates to medical devices, systems and methods and more particularly relates to post-operative wound closure devices, systems and treatment methods.

A combination of closed-suction drains and a NPWT system for deep post-operative wound closure can be beneficial. It may be desirable to have a system that includes drains to reach deep into surgical wounds with NPWT dressings at the wound surface. It may be beneficial if the drain could provide suction. It may be beneficial for the NPWT dressing to help close the wound. It may be beneficial for the wound to be closed around the drain. It may be desirable for devices, systems, and methods to eliminate the problem of the drain leaving a relatively large space between tissues that are normally anatomically connected (e.g. dead space). It may be desirable for devices, systems, and methods to eliminate the problem of the drain failing to provide a large surface area over which suction and/or irrigation can occur. Such a device may be beneficial for infection cases, spine surgeries, orthopedic fracture surgeries, plastic surgeries, or any other surgeries.

It may be desirable to provide deep-wound suction over a greater area. It may be desirable to provide complete wound irrigation at a local level. It may be desirable to deliver high-concentrations of local antibiotics to deep wounds. It may be desirable to promote wound closure with negative pressure. It may be desirable to treat post-operative wounds through a NPWT system without having to re-open the wound for component removal.

Any embodiment of the device may comprise an elongate shaft. Any embodiment of the device may comprise a wound dressing. Any embodiment of the device may comprise a removal element. The elongate shaft is preferably hollow, such as a tube, cannula, or catheter. The elongate shaft may have an external end disposed outside the patient and an internal end disposed in the patient's wound. The wound dressing may be an open pore, reticulated, hydrophobic foam sponge or may take any other form known in the art. The removal element may be a braid, cage, radially expandable member, or take any other form. The removal element may have any number of patterns but in preferred embodiments may be a helical braid with a distal end that is disposed in the wound and a trailing end that extends proximally outward toward a location external of the patient, away from the wound. The removal element may be collapsible. The distal end of the removal element may be of diameter or width greater than the elongate hollow tube in its expanded state. The distal end of the removal element may be of a diameter or width less than the lumen of the elongate hollow tube in its collapsed state. The distal end of the removal element may be a bulbous shape, cylindrical shape, or any other shape. The distal end of the removal element may conform to the contour of the wound dressing. The wound dressing may expand until constrained by the shape of the removal element. The internal end of the elongate shaft may abut the wound dressing. The removal element components may join to make up the trailing end. The trailing end of the removal element may span the length of the lumen of the elongate shaft, through the external end disposed outside the patient. The external end of the elongate shaft may connect to a suction and/or irrigation system with a fitting. The suction and/or irrigation system may be a NPWT system. The fitting may be a Luer lock or a custom fitting.

Optionally in any embodiment, the elongate shaft may have a y-split near the external end disposed outside the patient's wound, with two external arms. The first external arm end may connect to a suction and/or irrigation system with a fitting. The suction and/or irrigation system may be a NPWT system. The fitting may be a Luer lock or a custom fitting. A stopper of cylindrical shape may have a tight fit with the lumen of the elongate shaft. The stopper may have O-rings sized to maintain the negative-pressure seal in the elongate shaft. The stopper may reside in the second external arm of the elongate shaft. The removal element trailing end may extend past the second external arm end disposed outside the patient. The stopper may capture the trailing end of the removal element. The removal element may be captured by molding processes, mechanical mechanisms, bonding, or any other processes. The removal element may be pulled axially, causing the stopper to move accordingly.

Optionally in any embodiment, the elongate shaft may have a y-split near the external end disposed outside the patient's wound, with two external arms. One external arm end may connect to a suction and/or irrigation system with a fitting. The suction and/or irrigation system may be a NPWT system. The fitting may be a Luer lock or a custom fitting. An externally threaded cylindrical fitting may be bonded to the second external arm end. A cylindrical cap may have internal threads that mate with those of the fitting. The cap and the fitting threads may mate to maintain the negative-pressure seal in the elongate shaft. The removal element trailing end may extend into the second external arm of the elongate shaft, connecting to the threaded cap. The trailing end may connect to the threaded cap by molding processes, mechanical mechanisms, bonding, or any other processes. The cap may be unthreaded from the fitting, such that the removal element is pulled axially.

Optionally in any embodiment, the elongate shaft may have a y-split near the external end disposed outside the patient's wound, with two external arms. One external arm end may connect to a suction and/or irrigation system with a fitting. The suction and/or irrigation system may be a NPWT system. The fitting may be a Luer lock or a custom fitting. The outer diameter of the second external arm end may have cylindrical ratchets. The ratchets may be molded onto the elongate shaft or may be a fitting bonded onto the elongate shaft. A cylindrical cap may have a sliding fit with the ratcheted fitting. The cap may have an actuation mechanism that interfaces with the fitting ratchets. The actuation mechanism may be pushed to release the ratcheting to allow for axial movement. The cap and the fitting may maintain the negative-pressure seal in the elongate shaft. The cap may be moved axially along the fitting, such that the removal element is pulled axially.

Optionally in any embodiment, the elongate shaft may be multi-lumen. The elongate shaft may have one lumen that extends distally into the wound dressing. The extended lumen may have a closed tip or an open tip. The extended lumen may have a plurality of holes. The holes may be patterned axially and/or radially along the lumen. The holes may allow for removal of suctioned exudate along the length of the dressing. The holes may allow for distribution of irrigating fluids along the length of the dressing.

Optionally in any embodiment, the elongate shaft may be multi-lumen to provide separate pathways for suction and irrigation.

Optionally in any embodiment, there may be multiple elongate shafts that are connected along their length to provide separate pathways for irrigation and suction.

In some embodiments, there may be a series of wound dressings. The wound dressings may be captured in the removal element in order to fill a larger wound space.

Preferably the device may insert the wound dressing into the wound space of a clean wound for treatment. The elongate shaft may span from the wound bed to a suction and/or irrigation system disposed external of the patient. The wound may be closed around the elongate shaft. The device may be used with the external system to provide irrigation. The device may be used with the external system to suction exudates. The device may be used with the external system to instill antibiotics.

Preferably this device may remove the wound dressing after treatment through a closed-wound, without the need for a removal surgery. A removal mechanism may be used for device collapse and retraction. The trailing end of the removal element may be pulled axially, causing the distal end of the removal element to lengthen and narrow. The narrowed removal element may collapse the wound dressing. The trailing end of the removal element may continue to be pulled axially to retract the wound dressing into the elongate shaft. The device may be removed through a closed wound.

Optionally in any embodiment, the method for removal may include incremental collapse of the wound dressing with continued therapy.

Additional aspects of the invention will be apparent from the detailed descriptions and claims herein.

DETAILED DESCRIPTION OF THE INVENTION

Specific embodiments of the disclosed device, system and method of use will now be described with reference to the drawings. Nothing in this detailed description is intended to imply that any particular component, feature, or step is essential to the invention.

Figure 1A:
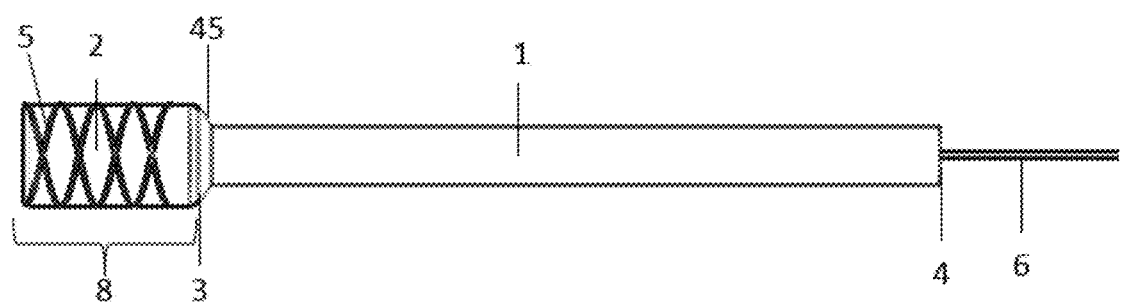
FIG. 1a shows a side view of an exemplary embodiment of a device for post-operative wound treatment having a removal element that encompasses a sponge, in accordance with some embodiments.
Figure 1B:
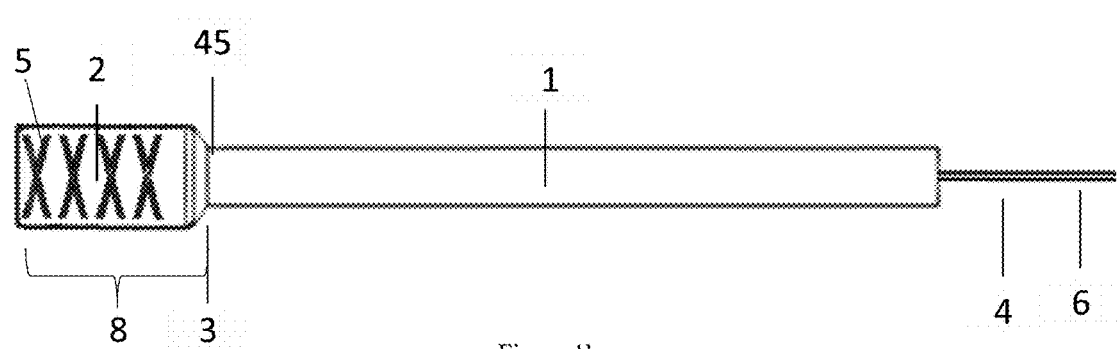
FIG. 1b shows a side view of an exemplary embodiment of a device for post-operative wound treatment having a removal element that is woven through a sponge, in accordance with some embodiments.
Figure 1C:
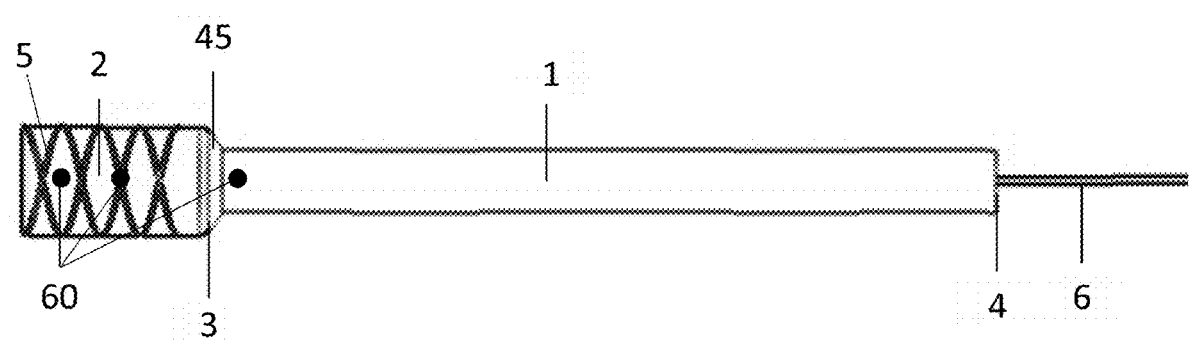
FIG. 1c shows a side view of an exemplary embodiment of a device for post-operative wound treatment having radiopaque markers on components of the device, in accordance with some embodiments.

FIGS. 1*a*-1*c* are a preferred embodiments of a device that may be used for post-operative wound treatment with an elongate shaft 1, wound dressing 2, and removal element 5. FIGS. 1*a*-1*c* each illustrate an embodiment with optional features, any of which may be used or substituted with other features in other embodiments discussed herein. In particular, FIG. 1*a* shows a side view of an exemplary embodiment of a device for post-operative wound treatment having a removal element that encompasses a sponge, in accordance with some embodiments. Additionally, FIG. 1*b* shows a side view of an exemplary embodiment of a device for post-operative wound treatment having a removal element that is woven through a sponge, in accordance with some embodiments. Further, FIG. 1*c* shows a side view of an exemplary embodiment of a device for post-operative wound treatment having radiopaque markers 60 on components of the device, in accordance with some embodiments.

As seen in FIGS. 1*a*-1*c*, the elongate shaft 1 may have an internal end 3 that is disposed in the patient's wound and an external end 4 that is disposed outside the patient. The elongate shaft 1 may be a tube, cannula, catheter, or other hollow structure preferably having a lumen extending the length thereof and that is sized to receive the wound dressing 2 and removal element 5 in a compressed configuration. As seen in FIGS. 1*a* and 1*c*, removal element 5 may be wrapped around wound dressing 2. As seen in FIG. 1*b*, removal element 5 may be woven through wound dressing 2. In some embodiments, wound dressing 2 may comprises a sponge. Further, as seen in FIG. 1*c*, elongate shaft 1, wound dressing 2, and removal element 5 may each comprise radiopaque markers.

The elongate shaft 1 may have a flared 45 internal end 3 to allow dressing guidance to be slidably advanced into the lumen during removal by proximal retraction of the removal element 5. The elongate shaft 1 may have a single lumen. Optionally, in any embodiment, the elongate shaft 1 may have multiple lumens in order to provide fluid suction and/or irrigation. For example, the elongate shaft 1 may have three lumens (one lumen for suction, one lumen for irrigation, and one lumen for device retraction) or the elongate shaft 1 may have three or more lumens (one or more lumens for suction, one or more lumens for irrigation, and one lumen for device retraction). The elongate shaft 1 preferably has a circular cross-section. Optionally, in any embodiment, the elongate shaft 1 may have various cross-sectional shapes known to those skilled in the art, such as an ovular cross-section or a rectangular cross-section. The elongate shaft 1 is preferably formed from a sterile flexible polymer. Any suitable material may be used including elastomeric or polymeric materials including, but not limited to, silicone or medical-grade polyvinyl chloride (PVC). The elongate shaft 1 is preferably formed from a uniform material. Optionally, in any embodiment, the elongate shaft 1 may have sections of varying durometer in order to control stiffness, flexibility or other mechanical properties of the elongate shaft 1. Optionally, in any embodiment, the elongate shaft 1 may be formed from multiple materials to provide desirable mechanical properties to the elongate shaft.

The wound dressing 2 is preferably a sterile, open cell reticulated, hydrophobic, polyurethane foam. The wound dressing 2 preferably has pore sizes of approximately 400 to 600 microns. Optionally, in any embodiment, the dressing 2 may have silver or antimicrobial agents added thereto. Optionally, in any embodiment, the dressing 2 may be non-open cell reticulated foam. Optionally, in any embodiment, the dressing 2 may be polyvinyl alcohol foam or any other material. Optionally, in any embodiment, the dressing 2 may have pore sizes of approximately 60 to 400 microns. Optionally, in any embodiment, the dressing 2 may have pore sizes that vary along the length of the dressing 2. Optionally, in any embodiment, the dressing 2 may have pore sizes that vary along the circumference of the dressing 2. Optionally, in any embodiment, the dressing 2 may have pore sizes that vary along any other direction. Optionally, in any embodiment, the dressing 2 may have multiple stacked layers with different materials to change the suction and dispersion properties of the dressing 2. For example, the dressing 2 may have a silver-coated polyurethane layer, a polyvinyl alcohol foam layer, and a waterproof adhesive layer. The stacked layers may be the same thickness or have varying thicknesses. The dressing 2 sizes may have surface areas up to 1000-1500 cm$^2$. The dressing 2 may be cylindrically shaped. Optionally, in any embodiment, the dressing 2 may be rectangular or another shape. The dressing 2 may have a long side (i.e. long length) and two short sides (i.e. small width and height). The dressing 2 may be collapsed with a narrowing of the width and height. Optionally, in any embodiment, the dressing 2 may be flexible so that it may be manipulated. The dressing 2 may be fabricated to allow equal distribution of negative pressure across the wound. The dressing 2 materials and configurations will be apparent to those skilled in the art and may vary depending on factors including patient's anatomy, exudate quantity, and/or state of the wound.

The removal element 5 may be a type of helical braid woven such that as the braid lengthens, it narrows. The removal element 5 may have a distal end 8 that is configured to be disposed in the wound and a trailing end 6 that extends proximally from the wound toward an external surface of the patient. The removal element 5 may be collapsible. The distal end 8 may be of diameter or width greater than the lumen of the elongate shaft 1 in its expanded state. The distal end 8 may be of diameter or width less than the lumen of the elongate shaft 1 in its collapsed state. Optionally, in any embodiment, the distal end 8 may conform to the wound dressing 2 contour. Optionally, in any embodiment, the distal end 8 may be bulbous, cylindrical, rectangular, or any other shape. The components of the removal element 5 may come together on one end of the distal end 8 to create a trailing end 6 which forms a tether that may be retracted proximally by a physician or other operator when removal is desired. The components may come together in a knot, be bonded together, or any other known processes of joining. The trailing end 6 may be a tight braid or bonded components that extend from distal end 8. Optionally, in any embodiment, the trailing end 6 may be a continuation of the distal end 8 helical braid.

The removal element 5 preferably encompasses the dressing 2 with a tight fit such that the dressing is entrapped by the removal element. Optionally, in any embodiment, the removal element 5 may be woven into the periphery of the dressing 2. Optionally, in any embodiment, the removal element 5 may be woven through the center of the dressing 2. Optionally, in any embodiment, the removal element 5 may be woven around the dressing 2, woven into the periphery of the dressing, and/or woven through the center of the dressing 2, or any combination thereof. The long-side of the dressing 2 may be aligned or substantially parallel with the removal element 5 longitudinal axis. The trailing end 6 of the removal element 5 may span the length of the elongate shaft 1 from the internal end 3, through the external end 4 with an additional length extending therepast that may be grasped by an operator or coupled to an actuation mechanism for retraction. The trailing end 6 may be pulled taut so that the removal element 5 captures the dressing 2 and also so that the internal end 3 of the elongate shaft 1 abuts the wound dressing 2. Optionally, in any embodiment, the elongate shaft 1 may be connected to the wound dressing 2 with adhesive or other method of bonding.

Figure 2A:
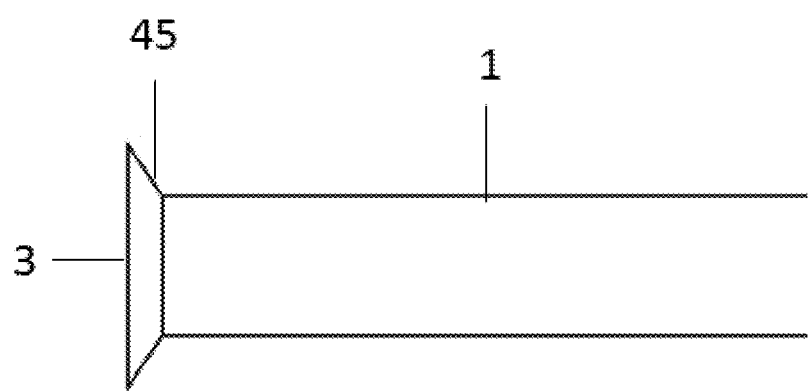
FIG. 2a shows a side view of an exemplary embodiment of the internal end of the elongate shaft, the internal end having a flare in accordance with some embodiments.
Figure 2C:
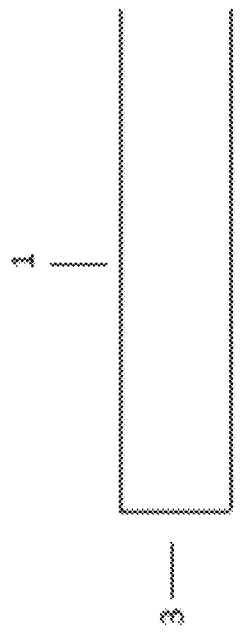
FIG. 2c shows a side view of an exemplary embodiment of the internal end of the elongate shaft, the internal end having no flare in accordance with some embodiments.
Figure 2B:
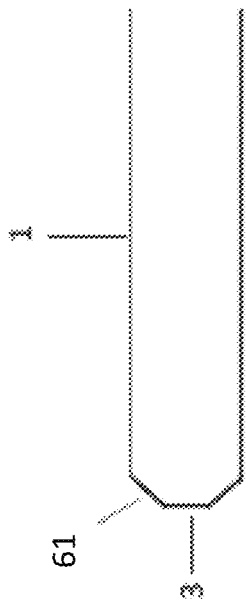
FIG. 2b shows a side view of an exemplary embodiment of the internal end of the elongate shaft, the internal end having an external chamfer in accordance with some embodiments.

FIG. 2a-2c are preferred embodiments of the elongate shaft 1, as depicted in FIG. 1 and may be used in this or any other embodiment of the device. In particular, FIG. 2a shows a side view of an exemplary embodiment of the internal end of the elongate shaft, the internal end having a flare in accordance with some embodiments. Additionally, FIG. 2b shows a side view of an exemplary embodiment of the internal end of the elongate shaft, the internal end having an external chamfer 61 in accordance with some embodiments. Further, FIG. 2c shows a side view of an exemplary embodiment of the internal end of the elongate shaft, the internal end having no flare in accordance with some embodiments.

The elongate shaft 1 preferably has a length of 0.5 m to 3 m. More preferably, the elongate shaft 1 has a length of 1 m to 2 m. The elongate shaft 1 preferably has an inner diameter of 2 mm to 10 mm. More preferably, the elongate shaft 1 has an inner diameter of 3 mm to 5 mm. The elongate shaft 1 preferably has an outer diameter of 4 mm to 15 mm. More preferably, the elongate shaft 1 has an outer diameter of 5 mm to 7 mm. The elongate shaft 1 may have a flared 45 internal end 3 to allow dressing guidance into the lumen during removal by proximal retraction of the dressing into the lumen of the elongate shaft 1. The flared diameter 45 is preferably 5 mm to 20 mm. More preferably, the flared diameter 45 is 7 mm to 15 mm. Optionally, in any embodiment and as illustrated in FIG. 2a, the flared 45 internal end 3 may be flexible so that it easily collapses as it is pulled through the wound during removal. Optionally, in any embodiment, the internal end 3 may be the same diameter as the rest of the elongate shaft 1. Optionally, in any embodiment and as illustrated in FIG. 2b, end 3 may have an external chamfer. Optionally, in any embodiment and as illustrate din FIG. 2c, end 3 may have no flare.

Figure 3A:
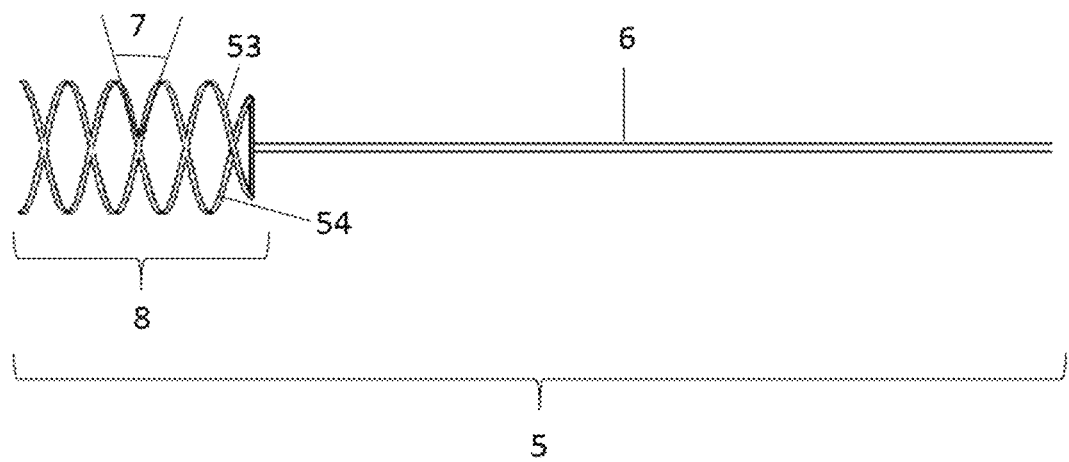
FIG. 3a shows a side view of an exemplary embodiment of the removal element, in accordance with some embodiments.
Figure 3B:
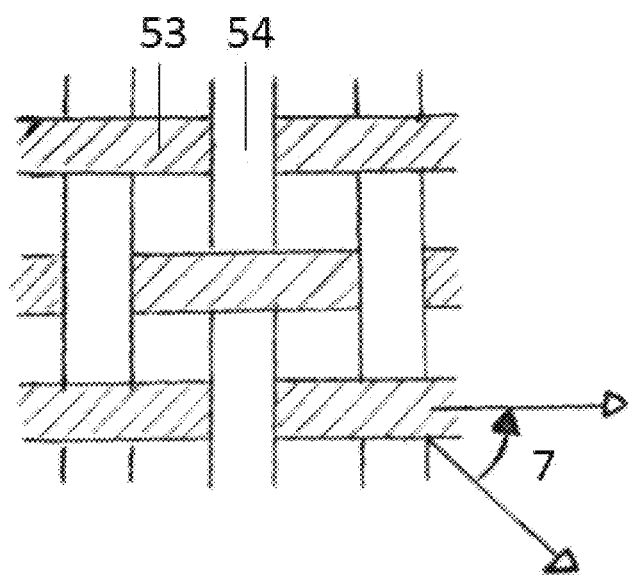
FIG. 3b shows a close-up of an exemplary embodiment of the removal element, in accordance with some embodiments.

FIG. 3a is a preferred embodiment of the removal element 5, as depicted in FIG. 1 and may be used in this or any other embodiment of the device. The removal element 5 may be a type of helical braid woven such that as the braid lengthens, it narrows due to the reduced angle 7 between the warp 53 and weft 54 components at their crossing points. The removal element 5 may be composed of any type of fiber, wire, or tube. Optionally, in any embodiment, the removal element 5 may be a cage, expandable member, or take any other form. The removal element 5 is preferably a biaxial braid. FIG. 3b shows a flat-version of a biaxial braid, as a preferred embodiment of the removal element shown in FIG. 3a. The removal element 5 may be composed of a plurality of intertwining components. The removal element 5 preferably is composed of between 4 and 16 intertwining components. More preferably, the removal element 5 is composed of 4 to 8 intertwining components. The fibers may be hollow. The removal element 5 may be woven in any pattern. The removal element 5 is preferably woven with pairs of warp 53 and weft 54 components that alternatively pass over and under each other, with one pair spiraling clockwise and the other pair spiraling counter-clockwise. The removal element 5 preferably has a 30 to 60-degree angle 7 between the warp 53 and weft 54 components. More preferably, the angle 7 between the warp 53 and weft 54 components is 40 to 50-degrees. The intertwining components are preferably flat with widths of 0.1 mm to 1 mm. More preferably, the intertwining components have widths of 0.1 mm to 0.3 mm. Optionally, in any embodiment, the removal element 5 may be multi-directional or unidirectional braids. Optionally, in any embodiment, the removal element 5 may have lower angle 7 orientations to change the expansion and compression properties of the removal element. Optionally, in any embodiment, the removal element 5 may have higher angle 7 orientations to change the expansion and compression properties of the removal element. The removal element 5 may be self-expanding. The removal element 5 may be sterile polypropylene fiber or any suitable fiber. The removal element 5 may be a flexible wire. The removal element 5 may have a trailing end 6 at one end that is of smaller diameter or width than the elongate shaft 1 (shown in FIG. 1). The distal end 8 may be woven to conform to the wound dressing 2 contour. The distal end 8 may have a bulbous shape that is slightly larger than the corresponding wound dressing 2. The distal end 8 may have a cylindrical shape or any other shape. The distal end 8 may be larger in diameter or width than the lumen of the elongate shaft 1 (shown in FIG. 1) in its expanded shape. The distal end 8 may be collapsible to a diameter or width smaller than the lumen of the elongate shaft 1 (shown in FIG. 1). The intertwining components of the removal element 5 may come together on a proximal portion of the distal end 8 to create a trailing end 6 that acts as a tether so the removal element may be pulled proximally. The intertwining components may come together in a knot, be bonded together, or any other known processes of joining, or they may be twisted or braided together to form a single tether. The trailing end 6 may be a tight braid or bonded components that extend proximally from the distal end 8. The trailing end 6 may have a circular cross-section. Optionally, in any embodiment, the trailing end 6 may have a rectangular cross-section forming a flat ribbon or any other shape. The trailing end 6 preferably has a diameter or maximum width of 0.1 mm to 1.2 mm. More preferably, the diameter or maximum width is 0.2 mm to 0.8 mm. The removal element 5 may be woven so that as the trailing end 6 is pulled axially, the circumference of the distal end 8 narrows and the distal end 8 collapses to engage and capture the dressing 2 (not pictured) so that as the removal element is retracted proximally it will also carry the dressing 2 with it in the proximal direction.

Figure 4A:
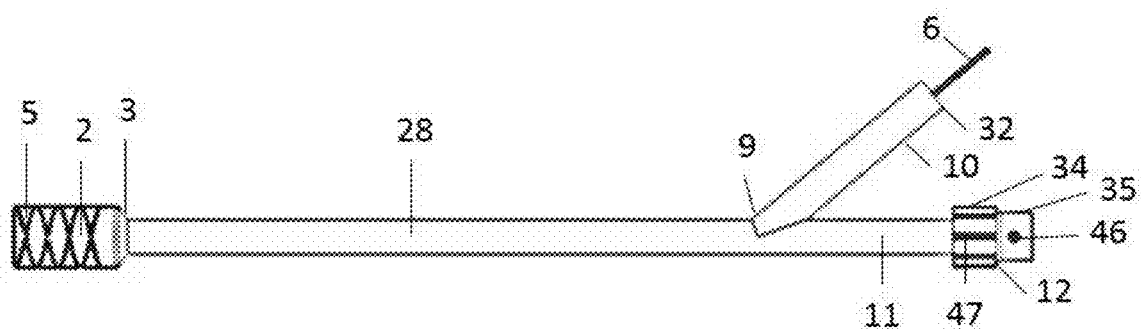
FIG. 4a shows a side view of another exemplary embodiment of a device for post-operative wound treatment with a y-split and stopper, in accordance with some embodiments.
Figure 4B:
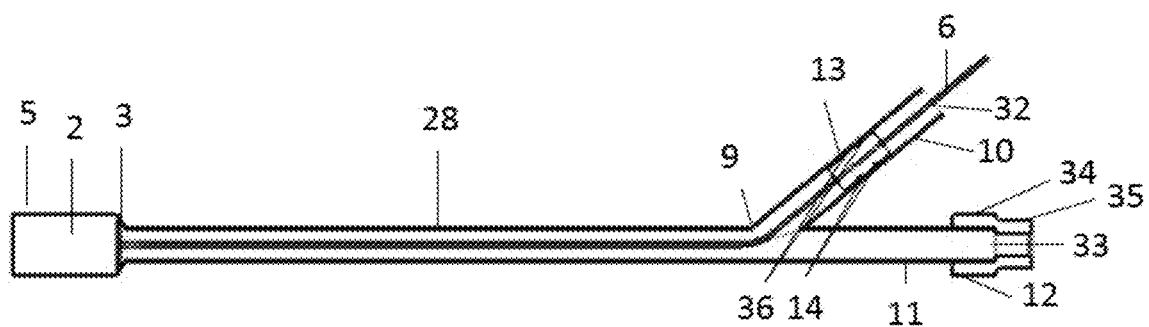
FIG. 4b shows a cross-section of another exemplary embodiment of a device for post-operative wound treatment with a y-split and stopper, in accordance with some embodiments.
Figure 4C:
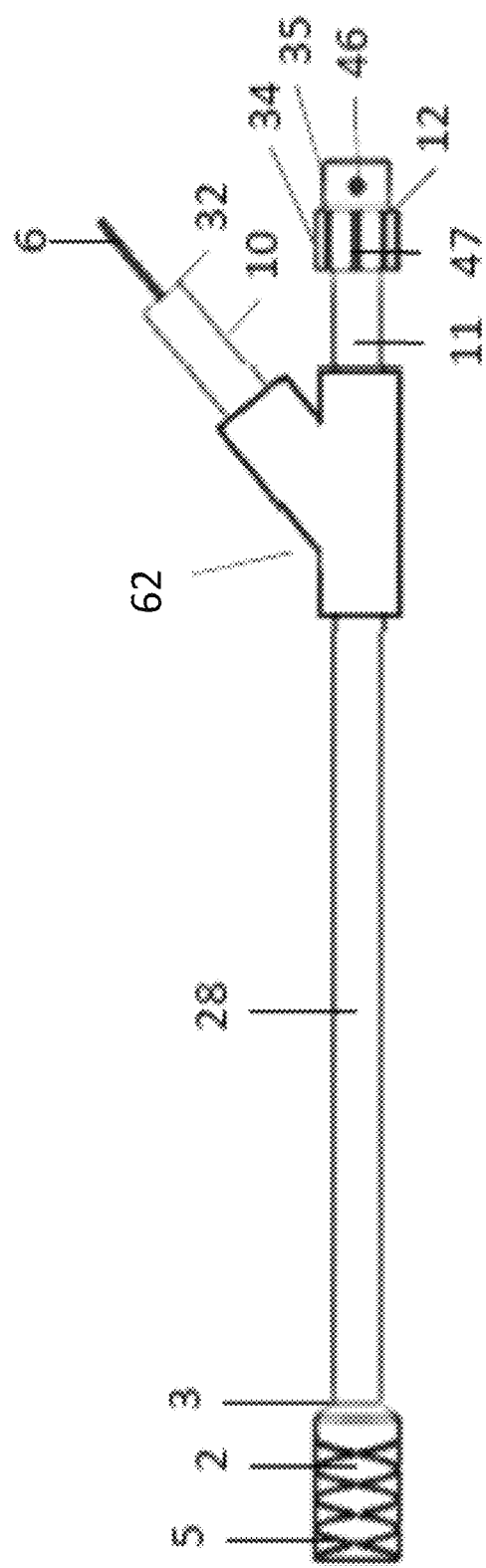
FIG. 4c shows a side view of another exemplary embodiment of a device for post-operative wound treatment with a y-fitting, in accordance with some embodiments.

FIGS. 4a and 4b and 4c each illustrate a preferred embodiment of a device that may be used for post-operative wound treatment with elongate shaft 28, wound dressing 2, removal element 5, external fitting 12, and stopper 13. FIG. 4a shows a side view of the embodiment and FIG. 4b shows a cross-section view of the embodiment. Additionally, FIG. 4c shows a side view of the embodiment having a y-fitting 62. FIGS. 4a and 4b and 4c each illustrate an embodiment with optional features, any of which may be used or substituted with other features in other embodiments discussed herein.

The elongate shaft 28 may have an internal end 3 that is disposed in the wound in the patient and a y-split 9 diverging into two external arms 10, 11 with two external ends 32, 33 preferably disposed outside of the wound and externally to the patient. Optionally, in any embodiment, the y-split 9 may be a t-split or any other divergence of one member into two. For example, the first external arm 11 may extend in a direction substantially parallel with the internal tubing axis and the second external arm 10 may diverge at a 20 to 60-degree angle. More preferably, the second external arm 10 diverges at a 30 to 40-degree angle. The elongate shaft 28 is preferably formed from a sterile flexible polymer. Any suitable material may be used including elastomeric or polymeric materials including, but not limited to, silicone or medical-grade polyvinyl chloride (PVC). The elongate shaft 28 preferably has an approximate length of 0.5 m to 3 m (from internal end to each external end). More preferably, the elongate shaft 28 has a length of 1 m to 2 m. Optionally, in any embodiment, the elongate shaft 28 may have any length to accommodate varying patient anatomy and use. The elongate shaft 28 preferably has an inner diameter of 2 mm to 10 mm. More preferably, the elongate shaft 28 has an inner diameter of 3 mm to 5 mm. The elongate shaft 28 preferably has an outer diameter of 4 mm to 15 mm. More preferably, the elongate shaft 28 has an outer diameter of 5 mm to 7 mm. The y-split 9 may allow the trailing end 6 of the removal element 5 to exit the external end 32 of the tubing without interfering with the connection to the external device for suction and irrigation.

The wound dressing 2 and removal element 5 may be the same as those described in FIG. 1.

The fitting 12 may be any medical tubing standard fitting known in the art such as a cylindrical shape. The fitting 12 may be configured to mate with commercial suction and/or irrigation device tubing. The fitting 12 outer diameter may be stepped. The fitting 12 preferably has a first outer diameter 34 of approximately 8 mm to 17 mm. More preferably, the fitting 12 has a first outer diameter 34 of 10 mm to 15 mm. The outer diameter 34 may have surface features such as ridges 47 around the circumference to help an operator grasp the fitting. The ridges 47 may have a square shape. Optionally, in any embodiment, the ridges 47 may be any shape. The ridges 47 preferably have widths of approximately 0.1 mm to 1 mm. More preferably, the ridges 47 have widths of 0.2 mm to 0.5 mm. The fitting 12 preferably has a second outer diameter 35 of approximately 5 mm to 13 mm. More preferably, the fitting 12 has a second outer diameter 35 of 7 mm to 10 mm. The second outer diameter 15 may have a locking pin 46 so that an external device female fitting can slide into the fitting 12 with the locking pin 46 entering a channel on the external fitting such that as the fitting is rotated, the locking pin 46 locks to the fitting. Optionally, in any embodiment, the outer diameter 35 may have any locking feature such as a threaded region as used in a Luer lock. The fitting 12 preferably has an inner diameter of 4 mm to 8 mm. More preferably, the fitting 12 has an inner diameter of 5 mm to 7 mm. The fitting 12 is preferably sterile acrylonitrile butadiene styrene (ABS) or another suitable polymer. Optionally, in any embodiment, the fitting 12 may be any suitable metal, ceramic, or other material.

A stopper 13 is preferably disposed in the opposite arm 10 of the y-split 9. The stopper 13 may be of cylindrical shape or any other shape. The stopper 13 preferably has a diameter of approximately 2 mm to 6 mm. More preferably, the stopper 13 has a diameter of 2.5 mm to 4.5 mm. The stopper 13 preferably has a length of 5 mm to 25 mm. More preferably, the stopper 13 has a length of 10 mm to 20 mm. The stopper 13 body is preferably sterile acrylonitrile butadiene styrene (ABS) or a comparable suitable polymer. Optionally, in any embodiment, the stopper 13 body may be any suitable metal, ceramic or other material. The stopper 13 preferably has multiple circumferential grooves 36 disposed therearound and sized to fit an external O-ring 14 in each. The circumferential grooves 36 may have rectangular cross-sections. Optionally, in any embodiment, the circumferential grooves 36 may be semi-circles or any shape. Optionally, in any embodiment, the stopper 13 may have other mechanical features to capture an O-ring 14. Optionally, in any embodiment, the O-rings 14 may be bonded to the stopper 13. The O-rings 14 preferably have outer diameters of approximately 2 mm to 6 mm. More preferably, the O-rings 14 have outer diameters of 3.1 mm to 5.1 mm. The O-rings 14 preferably have circular cross-sections. Optionally, in any embodiment, the O-rings 14 may have any shape cross-section. The O-rings 14 may have a press fit with the inner lumen of the arm 10 of the elongate shaft 28 to provide a seal. The O-rings 14 are preferably sterile rubber. Optionally, in any embodiment, the O-rings 14 may be any suitable elastomer.

The removal element 5 preferably encompasses the dressing 2 with a tight fit such that the dressing is entrapped by the removal element. The long-side of the dressing 2 may be aligned or substantially parallel with the removal element 5 longitudinal axis. The first external end 33 has a fitting 12 to connect to a suction and/or irrigation device canister tubing. The fitting 12 may be bonded to the external end 33 of the elongate shaft 28 using an adhesive. Optionally, in any embodiment, the fitting 12 may be connected to the external end 33 of the elongate shaft 28 by any bonding method including but not limited to mechanical bonding, chemical bonding, adhesives, ultrasound welding, solvent bonding, etc. The trailing end 6 of the removal element 5 spans the length of the lumen of the elongate shaft 28 from the internal end 3, through the second external arm 10, exiting through the second external end 32, disposed external to the patient. The trailing end 6 is pulled taut so that the removal element 5 captures the dressing 2 and also so that the internal end 3 of the elongate shaft 3 abuts the wound dressing 2. Optionally, in any embodiment, the elongate shaft 28 may be connected to the wound dressing 2 with adhesive or other method of bonding. A stopper 13 captures the trailing end 6 of the removal element 5 in the second external arm 10 of the elongate shaft 28 such that as the trailing end 6 is pulled axially, the stopper 13 also moves axially, allowing for removal element 5 collapse and subsequent collapse of the dressing 2 for device removal. The trailing end 6 may be captured by the stopper 13 during a molding process. Optionally, in any embodiment, the trailing end 6 may be captured by the stopper 13 by mechanical mechanisms or bonding. The stopper 13 may maintain the seal within the elongate shaft 28 through a press fit between the O-rings 17 and the inner lumen of the elongate shaft 28.

Figure 5:
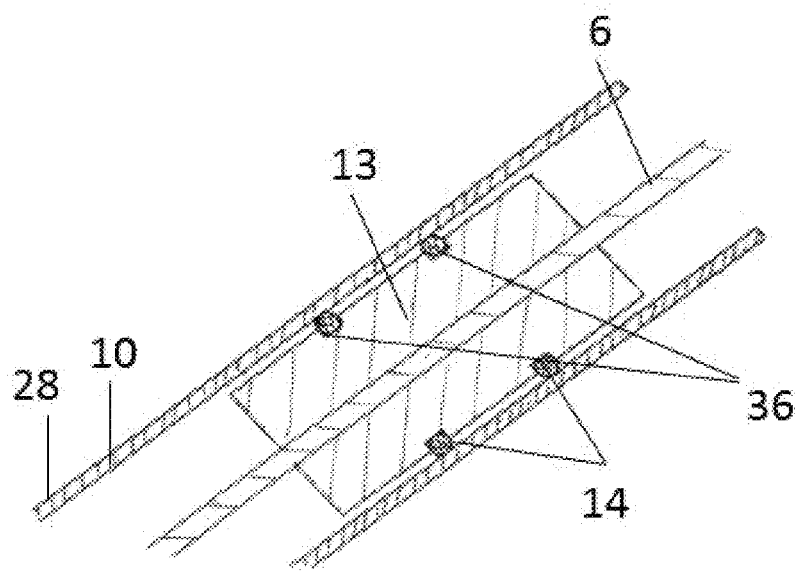
FIG. 5 shows a cross-section view of an exemplary embodiment of a stopper, in accordance with some embodiments.

FIG. 5 is a cross-section view of the stopper 13 as described in FIGS. 4a and 4b with multiple circumferential grooves 36 and multiple O-rings 14 to provide a press fit with the second external arm 10 of the elongate shaft 28.

Figure 6A:
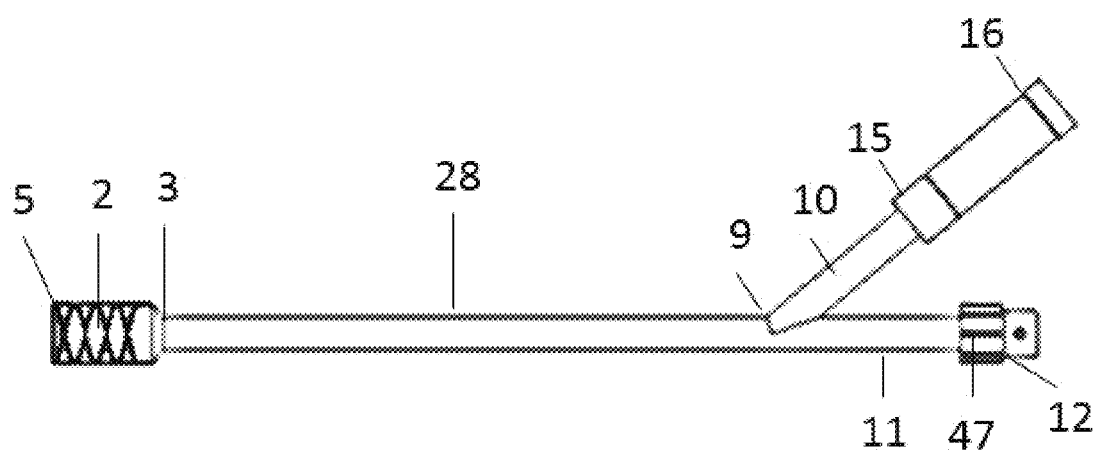
FIG. 6*a* shows a side view of another exemplary embodiment of a device for post-operative wound treatment with a y-split and threaded fitting, in accordance with some embodiments.
Figure 6B:
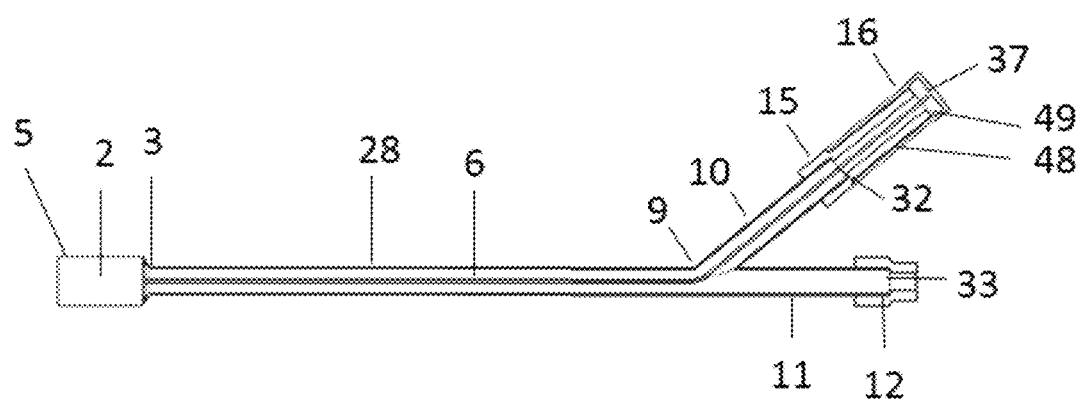
FIG. 6*b* shows a cross-section view of another exemplary embodiment of a device for post-operative wound treatment with a y-slit and threaded fitting, in accordance with some embodiments.

FIGS. 6a and 6b each illustrate a preferred embodiment of a device that may be used for post-operative wound treatment with elongate shaft 28, wound dressing 2, removal element 5, external fitting 12, threaded fitting 15, and threaded cap 16. FIG. 6a shows a side-view of the embodiment and FIG. 6b shows a cross-sectioned view of the embodiment. FIGS. 6a and 6b each show the elongate shaft 28 with y-split 9 and external fitting 12 on one external arm 11 as described in FIGS. 4a and 4b and the wound dressing 2 and removal element 5 as described in FIG. 1. FIGS. 6a and 6b each illustrate an embodiment with optional features, any of which may be used or substituted with other features in other embodiments discussed herein.

The externally threaded fitting 15 is preferably of cylindrical shape. The fitting 15 preferably has an inner diameter of approximately 4 mm to 8 mm. More preferably, the fitting 15 has an inner diameter of 5 mm to 7 mm. The fitting 15 preferably has an external diameter of 6 mm to 10 mm. More preferably, the fitting 15 has an external diameter of 7 mm to 9 mm. The internally threaded cap 16 is preferably of cylindrical shape. Optionally, in any embodiment, the cap 16 may be any shape. The cap 16 preferably has a cylindrical lumen sized to mate with the externally threaded fitting 15. The fitting 15 preferably has external threads 48 along a portion of the length of the tubular body. Optionally, in any embodiment, the fitting 15 may be threaded along its entire length. The cap 16 preferably has internal threads 49 along a portion of the length of the tubular body. Optionally, in any embodiment, the cap 16 may be threaded along its entire length. The fitting 15 length is preferably 5 mm to 100 mm. More preferably, the fitting 15 length is 5 mm to 20 mm. The cap 16 length is preferably 5 mm to 100 mm. More preferably, the cap 16 length is 5 mm to 20 mm. The trailing end 6 of the removal element 5 may be attached to the inner end 37 of the cap 16 by being molded into it. Optionally, in any embodiment, the trailing end 6 may be attached to the cap 16 by any mechanical mechanism or bonding. The fitting 15 is preferably acrylonitrile butadiene styrene (ABS). Optionally, in any embodiment, the fitting 15 is any suitable polymer. The cap 16 is preferably acrylonitrile butadiene styrene (ABS). Optionally, in any embodiment, the cap 16 is any suitable polymer.

The removal element 5 preferably encompasses the dressing 2 with a tight fit such that the dressing is entrapped by the removal element. The long-side of the dressing 2 may be aligned or substantially parallel with the removal element 5 longitudinal axis. The first external end 33 may have a fitting 12 to connect to suction and/or irrigation device canister tubing. The fitting 12 may be bonded to the external end 33 of the elongate shaft 28 using adhesive. Optionally, in any embodiment, the fitting 12 may be connected to the external end 33 of the elongate shaft 28 by any bonding method. The second external end 32 may have an externally threaded fitting 15. The fitting 15 may be bonded to the second external end 32 using adhesive. Optionally, in any embodiment, the fitting 15 may be bonded to the second external end 32 by any bonding method. The trailing end 6 of the removal element 5 may span the length of the lumen of the elongate shaft 28 from the internal end 3, through the second external arm 10, through the second external end 32, to attach to the internally threaded cap 16. As the cap 16 is unscrewed from the fitting 15, the trailing end 6 of the removal element 5 is pulled axially. The trailing end 6 may be pulled taut by unthreading the cap 16 so that the removal element 5 captures the dressing 2 and also so that the internal end 3 of the elongate shaft 28 abuts the wound dressing 2. Optionally, in any embodiment, the elongate shaft 28 may be connected to the wound dressing 2 with adhesive or other method of bonding. The fitting 15 and cap 16 may have mating threads 48, 49 so that when engaged, a seal is maintained within the elongate shaft 28.

Figure 7:
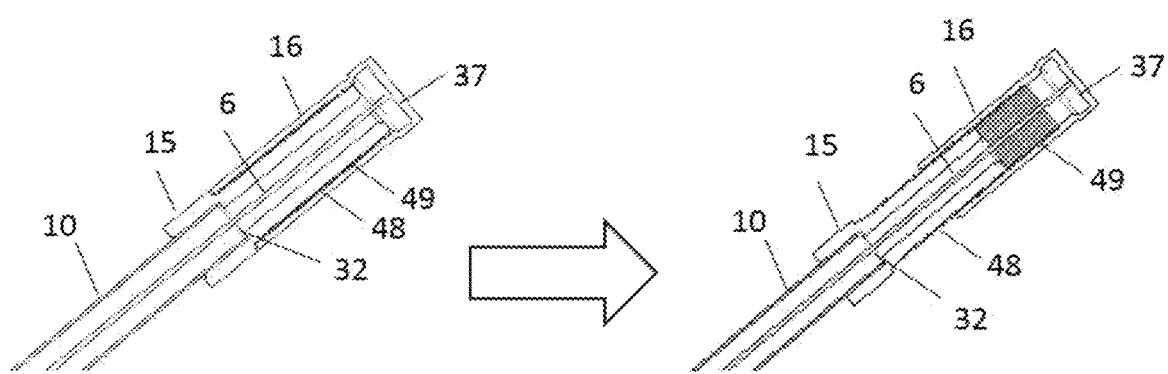
FIG. 7 shows a cross-section view of an exemplary embodiment of the external end threaded fitting and cap, in accordance with some embodiments.

FIG. 7 is a preferred embodiment of the externally threaded fitting 15 and the internally threaded cap 16, as described in FIG. 6. The fitting 15 attaches to the end 32 of one external arm 10. The fitting 15 and cap 16 may have mating threads 48, 49. The trailing end 6 of the removal element (not fully pictured) may attach to the inner end 37 of the cap 16. As the cap 16 is unscrewed from the fitting 15, the trailing end 6 of the removal element is pulled axially thereby pulling the dressing (not pictured) out of the wound into the elongate shaft 28.

Figure 8:
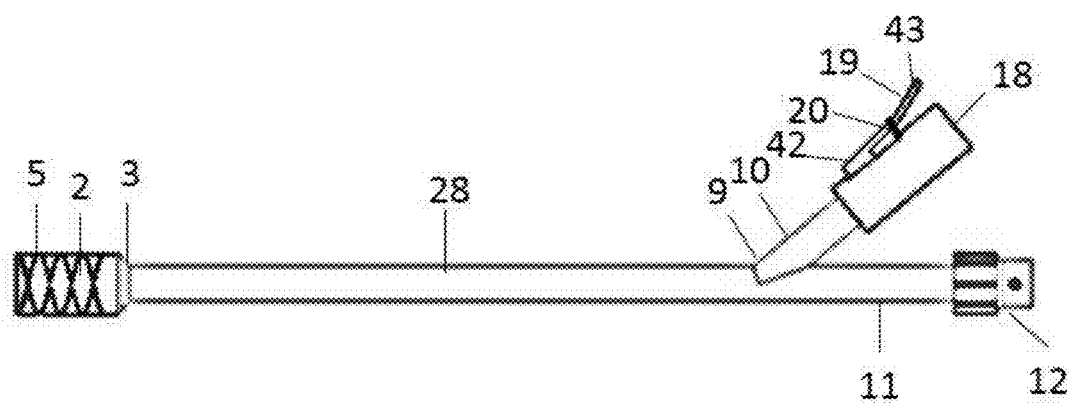
FIG. 8 shows a side view of another exemplary embodiment of a device for post-operative wound treatment with y-split and ratcheted fitting, in accordance with some embodiments.

FIG. 8 is a preferred embodiment of a device that may be used for post-operative wound treatment with elongate shaft 28, wound dressing 2, removal element 5, external fitting 12, ratcheted fitting 17, and cap 18. FIG. 8 shows the elongate shaft 28 with y-split 9 and external fitting 12 on one external arm 11 as described in FIGS. 4a and 4b and the wound dressing 2 and removal element 5 as described in FIG. 1. FIG. 6 illustrates an embodiment with optional features, any of which may be used or substituted with other features in other embodiments discussed herein.

The ratcheted fitting 17 may be bonded to one external arm 10 of the elongate shaft 28. The ratcheted fitting 17 is preferably of cylindrical shape. Optionally, in any embodiment, the ratcheted fitting 17 may be any shape. The fitting 17 may have an inner diameter of approximately 5 to 7 mm. The fitting 17 preferably has ratchets 39 along a portion of the length of the tubular body. Optionally, in any embodiment, the fitting 17 may have ratchets (not pictured) along its entire length. The ratchet fitting 17 length is preferably 5 mm to 100 mm. More preferably, the fitting 17 length is 5 mm to 20 mm. The ratchet cap 18 is preferably of cylindrical shape. Optionally, in any embodiment, the ratchet cap 18 may be any shape. The cap 18 preferably has an inner diameter that provides for a sliding fit with the fitting 17. The cap 18 length is preferably 5 mm to 100 mm. More preferably, the cap 18 length is 5 mm to 20 mm. The ratchet cap 18 preferably has an actuatable arm 19 that is rotated about a pin 20. Optionally, in any embodiment, the cap 18 may also have an actuation mechanism 19 that moves by any mechanism such as a button, a lever, or any other mechanism. The actuation mechanism 19 may be an elongate rectangular shape with two ends 42, 43 on opposite sides of the pin 20. Optionally, in any embodiment, the actuation mechanism 19 may be any shape. The trailing end 6 of the removal element 5 may be attached to the inner end 40 of the cap 18 by being molded into it. Optionally, in any embodiment, the trailing end 6 may be attached to the cap 18 by any mechanical mechanism or bonding. The fitting 17 is preferably sterile acrylonitrile butadiene styrene (ABS). Optionally, in any embodiment, the fitting 17 may be any suitable polymer. The cap 18 is preferably sterile acrylonitrile butadiene styrene (ABS). Optionally, in any embodiment, the cap 18 may be any suitable polymer. The cap 18 is able to move axially along the fitting 17 when the actuation mechanism 19 is disengaged, pulling the trailing end 6 of the biaxial braid 5 axially thereby pulling the dressing 2 out of the wound into the elongate shaft 28.

The removal element 5 preferably encompasses the dressing 2 with a tight fit such that the dressing is entrapped by the removal element. The long-side of the dressing 2 may be aligned or substantially parallel with the removal element 5 longitudinal axis. The first external end 33 may have a fitting 12 to connect to suction and/or irrigation device canister tubing. The fitting 12 may be bonded to the external arm 10 of the elongate shaft 28 using adhesive. Optionally, in any embodiment, the fitting 12 may be bonded by any bonding method. The second arm 10 has a ratcheted fitting 17. The fitting 17 may be bonded using adhesive. Optionally, in any embodiment, the fitting 17 may be bonded by any bonding method. The trailing end (not pictured) of the removal element 5 may span the length of the lumen of the elongate shaft 28 from the internal end 3, through the second external arm 10, through the second external end (not pictured) disposed external to the patient, to attach to the ratchet cap 18. The trailing end may be pulled taut so that the removal element 5 captures the dressing 2 and also so that the removal element 5 captures the dressing 2 and also so that the internal end 3 of the elongate shaft 28 abuts the wound dressing 2. Optionally, in any embodiment, the elongate shaft 28 may be connected to the wound dressing 2 with adhesive or other method of bonding. The cap 18 actuation mechanism 19 may disengage, enabling the cap 18 to move axially, pulling the trailing end of the biaxial braid 5 axially thereby pulling the dressing 2 out of the wound into the elongate shaft 28.

Figure 9:
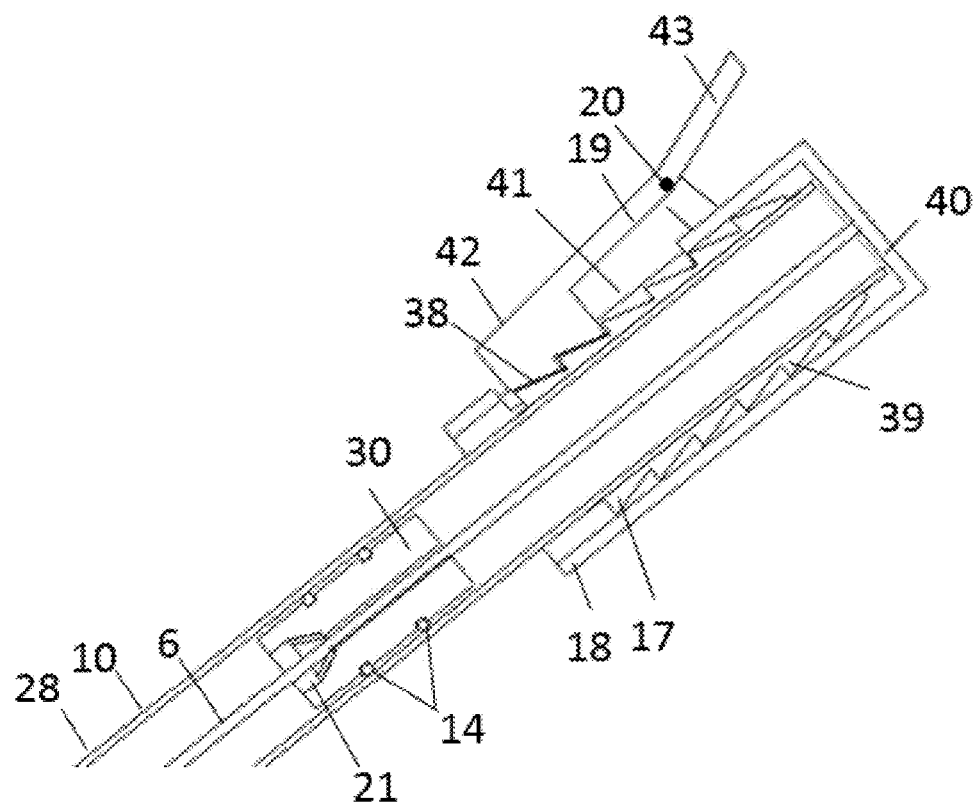
FIG. 9 shows a cross-section view of an exemplary embodiment of the external end ratcheted fitting and cap, in accordance with some embodiments.

FIG. 9 is a preferred embodiment of the ratcheted fitting 17 and cap 18 from FIG. 8. The cap 18 may have a cutout 41 that the actuation mechanism 19 can rotate into, about pin 20. The actuation mechanism 19 may have one or more ratchets 38 on one end 42. The actuation mechanism 19 may have ratchets 38 on one end 42. The ratchets 38 may be shaped to engage with the fitting ratchets 39. The actuation mechanism 19 ratchets 38 and fitting ratchets 39 may be a triangular shape or form steps. The pitch of the ratchets 38, 39 may be adjusted to any desired spacing in order to control coarseness or fineness of adjustment. Optionally, in any embodiment, the actuation mechanism 19 ratchets 38 and fitting ratchets 39 may be any mating shape. The cap 18 is able to move axially along the fitting 17 when the actuation mechanism 19 is disengaged by pushing on one end 43, pulling the trailing end 6 of the biaxial braid (not fully pictured) axially thereby pulling the dressing (not pictured) out of the wound into the elongate shaft 28.

Optionally in any embodiment, the external ratchets 39 may be molded as part of the external surface of the second external arm 10 of the elongate shaft 28.

Optionally in any embodiment, there may be a stopper 30 in the inner lumen of the second external arm 10 of the elongate shaft 28, as described in FIGS. 4a and 4b. The stopper 30 maintains the pressure seal in the elongate shaft 28.

Optionally, in any embodiment, the stopper 30 may also have a cone-shaped custom O-ring 21. The O-ring 21 preferably has an inner diameter of 0.1 to 0.8 mm. The O-ring 21 may be captured in the stopper 30 by bonding or adhesive. Optionally, in any embodiment, the O-ring 21 may be captured by any mechanical feature. The axis of the O-ring 21 may be aligned with the center axis of the stopper 30. The trailing end 6 of the removal element (not fully pictured) may be able to pass through the center axis of the stopper 30 and custom O-ring 21 while maintaining the seal with a tight fit between the trailing end 6 and the O-ring 21.

The cap 18 actuation mechanism 19 may disengage to cause the cap ratchets 38 to release the fitting ratchets 39, enabling the cap 18 to move axially, pulling the trailing end 6 of the biaxial braid (not pictured) axially thereby pulling the dressing (not pictured) out of the wound into the elongate shaft 28.

Figure 10:
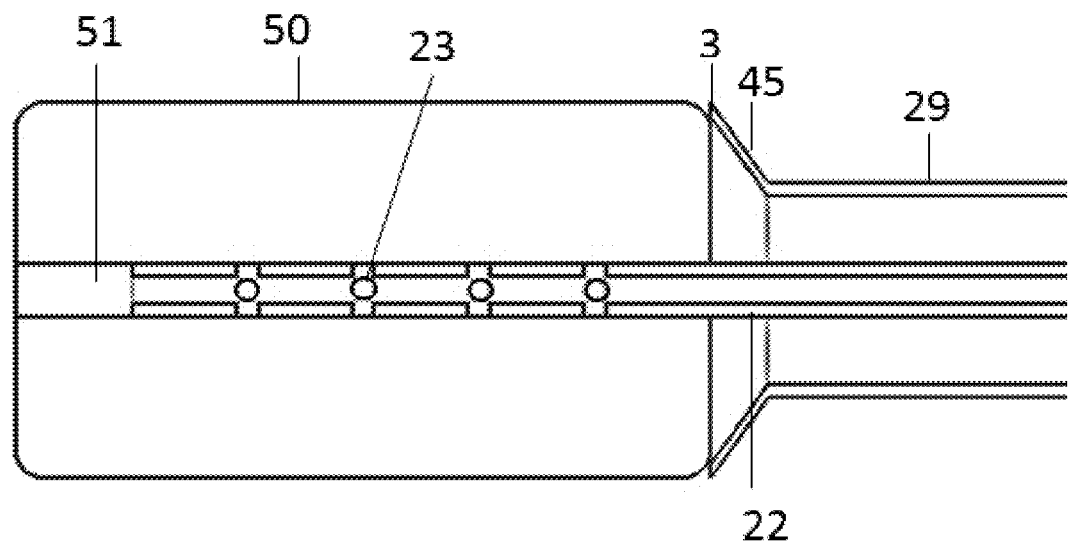
FIG. 10 shows a cross-section of another exemplary embodiment with a multi-lumen elongate shaft, one lumen extending proximally into the wound dressing, in accordance with some embodiments.

FIG. 10 is a preferred embodiment of the internal end 3 of a multi lumen elongate shaft 29 and a cannulated wound dressing 50 with the removal element removed for convenient illustrative purposes although it is appreciated that the removal element is preferably included. The elongate shaft 29 may have two members, one that is connected to an inlet and one that is connected to an outlet. Each of the two members may be movable relative to one another. The two members may comprise a same material. The two members may comprise a similar material. The two members may be bonded together with adhesive. The two members may be bonded together using any known bonding process. The internal end 3 is flared to allow guidance into the lumen, as described in FIG. 2.

The wound dressing 50 is preferably a sterile, open cell reticulated, hydrophobic, polyurethane foam. The wound dressing 50 preferably has pore sizes of approximately 400 to 600 microns. Optionally, in any embodiment, the dressing 50 may have silver or antimicrobial additions. Optionally, in any embodiment, the dressing 50 may be non-open cell reticulated foam. Optionally, in any embodiment, the dressing 50 may be polyvinyl alcohol foam. Optionally, in any embodiment, the dressing 50 may have pore sizes of approximately 60 to 400 microns. Optionally, in any embodiment, the dressing 50 may have multiple layers with different materials to change the suction and dispersion properties of the dressing 50. For example, the dressing 50 may have a silver-coated polyurethane layer, a polyvinyl alcohol foam layer, and a waterproof adhesive layer. The stacked layers may be the same thickness or have varying thicknesses. Dressing 50 sizes may have surface areas up to 1000-1500 cm$^2$. The dressing 50 may be cylindrically shaped. Optionally, in any embodiment, the dressing 50 may be rectangular or another shape. The dressing 50 may have a long side (i.e. long length) and two short sides (i.e. small width and height). The dressing 50 may be collapsed with a narrowing of the width and height. The dressing 50 may be cannulated through the center axis, along the long side, to allow for a hollow shaft to pass through. The cannula 51 may extend through the entire dressing 50. Optionally, in any embodiment, the cannula 51 may extend only partially through the dressing 50. Optionally, in any embodiment, the dressing 50 may be flexible so that it may be manipulated. The dressing 50 may be fabricated to allow equal distribution of negative pressure across the wound. The dressing 50 materials and configurations will be apparent to those skilled in the art and may vary depending on factors including patient's anatomy, exudate quantity, and/or state of the wound.

The elongate shaft 29 may have an internal end 3 that is disposed in the patient's wound and an external end (not pictured) that is disposed outside the patient. The elongate shaft 29 may be a tube, cannula, catheter, or other hollow structure that is sized to receive the wound dressing 50 and removal element in a compressed configuration. The elongate shaft 29 may have a flared 45 internal end 3 to allow dressing guidance to be slidably advanced into the lumen during removal by proximal retraction of the removal element 5. Optionally, in any embodiment, the elongate shaft 29 may have various cross-sectional shapes known to those skilled in the art, such as an ovular cross-section or a rectangular cross-section. The elongate shaft 29 is preferably formed from a sterile flexible polymer. Any suitable material may be used including elastomeric or polymeric materials including, but not limited to, silicone or medical-grade polyvinyl chloride (PVC). The elongate shaft 29 is preferably formed from a uniform material. Optionally, in any embodiment, the elongate shaft 29 may have sections of varying durometer in order to control stiffness, flexibility or other mechanical properties of the elongate shaft 29. Optionally, in any embodiment, the elongate shaft 29 may be formed from multiple materials to provide desirable mechanical properties to the elongate shaft.

A piece of tubing from one of the lumens from the elongate shaft 29 extends distally from the internal end 3 to form a hollow extension 22. The hollow extension 22 is preferably tubular with a diameter of 0.5 mm to 5 mm. More preferably, the hollow extension 22 diameter is 1 mm to 3 mm. Optionally, in any embodiment, the hollow extension 22 may have any shape. For example, the lumen of the elongate shaft 29 may be divided into two equal lumens down with the hollow extension 22 having a D-shaped half-circle cross-section. The hollow extension 22 may extend internally into the wound dressing 50. The hollow extension 22 may extend distally the length of the wound dressing 50. Optionally, in any embodiment, the hollow extension 22 may extend distally partially across the wound dressing 50. The hollow extension 22 may have an open proximal tip. Optionally, in any embodiment, the hollow extension 22 may have a closed tip. The hollow extension 22 may have a plurality of holes 23 distributed circumferentially. The hollow extension 22 may have a plurality of holes 23 distributed axially. Optionally, in any embodiment, the hollow extension 22 may have a plurality of holes 23 distributed circumferentially and axially in any pattern. The plurality of holes 23 may provide more distributed suctioning of exudates and/or distribution of irrigating fluids. The holes 23 preferably have a diameter of 0.1 mm to 1.5 mm. More preferably, the holes 23 have a diameter of 0.2 mm to 0.8 mm in diameter. Optionally, in any embodiment, the holes 23 may be various sizes. The hollow extension 22 is preferably of the same material as the body of the elongate shaft 29. Optionally, in any embodiment, the hollow extension 22 is a different material than that of the elongate shaft 29. Optionally, in any embodiment, the hollow extension 22 is a different durometer than that of the elongate shaft 29.

Figure 11:
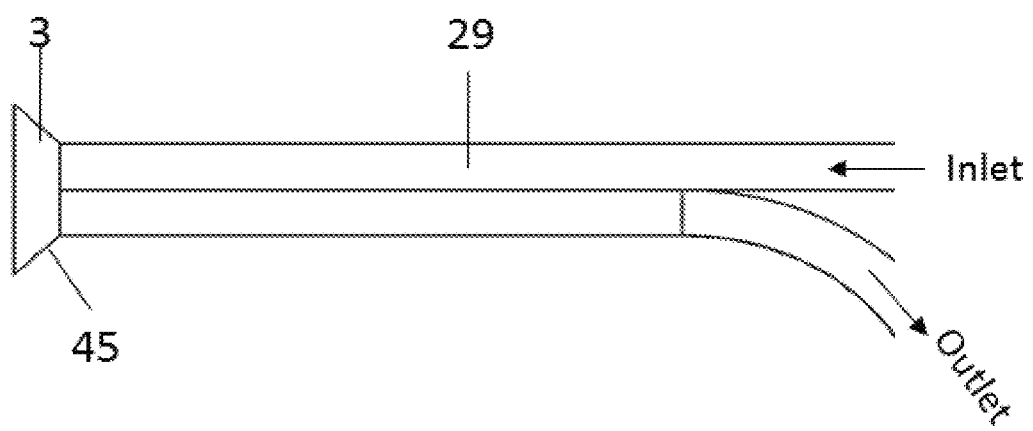
FIG. 11 shows a side view of another exemplary embodiment of the elongate shaft with separate irrigation and suction channels, in accordance with some embodiments.

With reference to FIG. 11, in one embodiment, there may be two identical elongate shafts 29 that are bonded together along their length. The elongate shafts 29 may be bonded together with adhesive or any processes of bonding. The elongate shaft 29 may have a flared 45 internal end 3. The elongate shafts 29 may be a tube, cannula, catheter, or other hollow structure. The elongate shafts 29 may have a single lumen extending the length of the shaft. The elongate shafts 29 may have a circular cross-section. The elongate shafts 29 may be a sterile flexible polymer or other material. The identical elongate shafts 29 may be pulled apart for convenience while attaching to an external system for separate inlet and outlet channels, one for suction and one for irrigation. The removal element (not pictured) may span either channel. Alternatively, the construct of the two elongate shafts may be co-extruded to form a single integral component with two lumens/channels.

Figure 12:
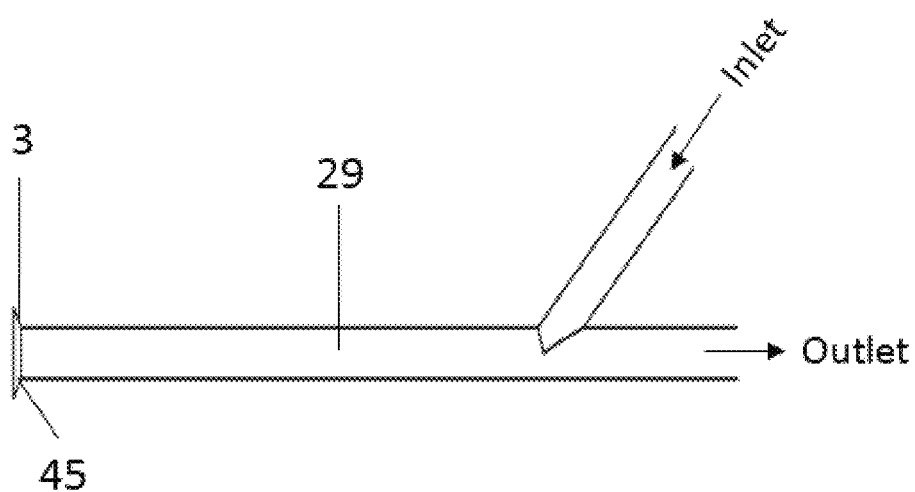
FIG. 12 shows a side view of another exemplary embodiment of the elongate shaft with separate irrigation and suction channels, in accordance with some embodiments.

With reference to FIG. 12, in one embodiment, there is one elongate shaft 29 with a y-connection that allows for two end-connections to external system tubing, one for inlet and the other for outlet, one for suction and one for irrigation. The removal element (not pictured) may span either channel. The elongate shafts 29 may have a flared 45 internal end 3. The elongate shafts 29 may be a tube, cannula, catheter, or other hollow structure. The elongate shafts 29 may have a single lumen that span the length of the shaft. The elongate shafts 29 may have a circular cross-section. The elongate shafts 29 may be a sterile flexible polymer or any material.

Figure 13:
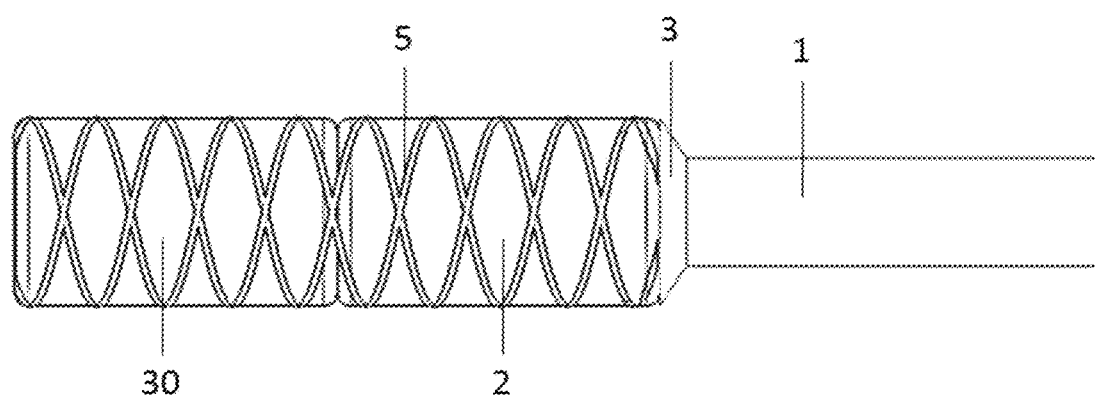
FIG. 13 shows a side view of another exemplary embodiment of a series of wound dressings captured by the removal element, in accordance with some embodiments.

FIG. 13 is a preferred embodiment of a series of wound dressings 2, 30 captured by the removal element 5 to fill a larger wound space. Optionally, in any embodiment, wound dressings 2, 30 in various configurations may be captured by the removal element 5. The elongate shaft 1 and removal element 5 may be the same as those previously described in FIG. 1. The wound dressings 2, 30 may be a sterile, open cell reticulated, hydrophobic, polyurethane foam. The wound dressings 2, 30 may have pore sizes of approximately 400 to 600 microns. Optionally, in any embodiment, the dressings 2, 30 may be polyvinyl alcohol foam or any other material.

Optionally, in any embodiment, the dressings 2, 30 may have pore sizes of approximately 60 to 400 microns. Optionally, in any embodiment, the dressings 2, 30 may have pore sizes that vary along the length of the dressings 2, 30. Optionally, in any embodiment, the dressings 2, 30 may have pore sizes that vary along the circumference of the dressings 2, 30. Optionally, in any embodiment, the dressings 2, 30 may have pore sizes that vary along any other direction. Optionally, in any embodiment, the dressings 2, 30 may have multiple stacked layers with different materials to change the suction and dispersion properties of the dressings 2, 30. For example, the dressings 2, 30 may have a silver-coated polyurethane layer, a polyvinyl alcohol foam layer, and a waterproof adhesive layer. The stacked layers may be the same thickness or have varying thicknesses. The dressings 2, 30 sizes may have surface areas up to 500-1500 cm$^2$. The dressings 2, 30 may be cylindrically shaped. Optionally, in any embodiment, the dressings 2, 30 may be rectangular or another shape. The dressings 2, 30 may have a long side (i.e. long length) and two short sides (i.e. small width and height). The dressings 2, 30 may be collapsed with a narrowing of the width and height. The dressings 2, 30 may be flexible so that they may be manipulated. The dressings 2, 30 may be fabricated to allow equal distribution of negative pressure across the wound. The removal element 5 may encompasses the dressings 2, 30 with a tight fit such that the dressing is entrapped by the removal element. The long-side of the dressings 2, 30 may be aligned or substantially parallel with the removal element 5 longitudinal axis. Operation of the device in FIG. 13 is generally the same as previously described in other embodiments. Retraction of the removal element 5 collapses the removal element 5 and captures the dressings 2, 30 which are then pulled into the internal end 3 of the elongate shaft 1 which can then be easily removed from the patient without requiring removal surgery.

Figure 14:
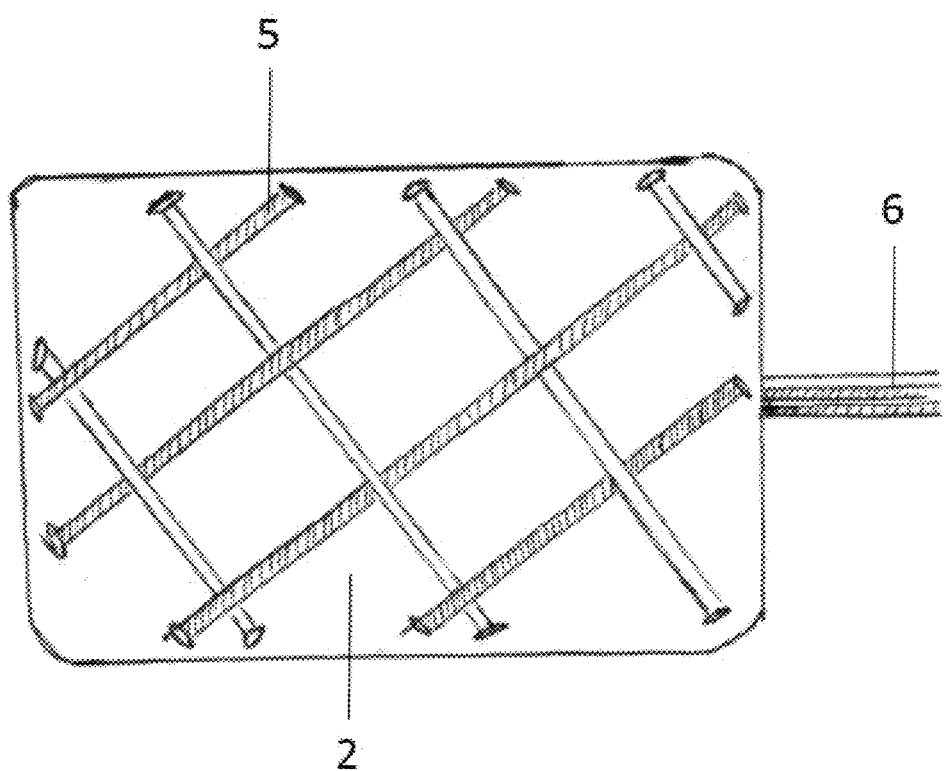
FIG. 14 shows a side view of another exemplary embodiment of a removal element woven into a wound dressing, in accordance with some embodiments.

FIG. 14 is a preferred embodiment of the removal element 5 being intertwined into the wound dressing 2 with the elongate shaft removed for convenient illustrative purposes although it is appreciated that the elongate shaft is preferably included. The removal element 5 may be the same as that described in FIG. 1. The removal element 5 may be a helical braid, such as a biaxial braid, with a trailing end 6. Optionally, in any embodiment, the removal element 5 may be woven into the periphery of the dressing 2. Optionally, in any embodiment, the removal element 5 may be woven through the center of the dressing 2. Optionally, in any embodiment, the removal element 5 may be woven around the dressing 2, woven into the periphery of the dressing, and/or woven through the center of the dressing 2, or any combination thereof.

Figure 15:
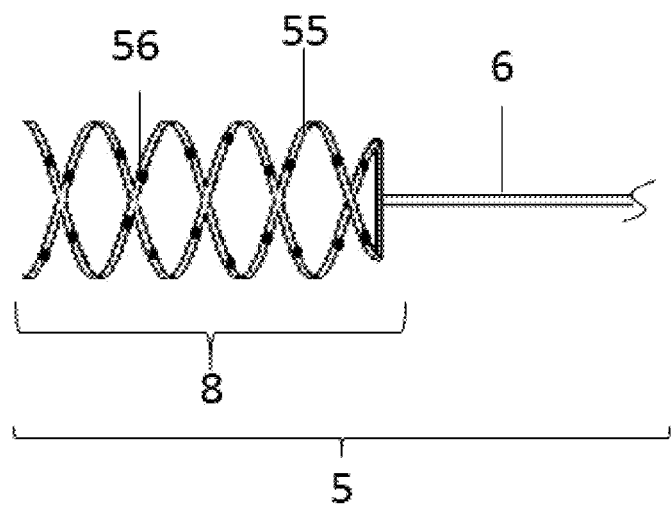
FIG. 15 shows a side view of another exemplary embodiment of the removal element composed of hollow components, in accordance with some embodiments.

FIG. 15 is a preferred embodiment of the removal element 5, as shown in FIGS. 3a and 3b, composed of hollow components 55. The hollow components 55 may be tubular or any shape. The hollow components 55 may be any type of fiber, metal, or other material. The hollow components 55 may be flexible. The hollow components 55 may have a plurality of ports 56 located along the length of the component at the distal end 8. The ports 56 may be holes. The ports 56 may be mesh. The ports 56 may be any other form that allows for fluid diffusion. Antibiotics may be distilled from the trailing end 6 (proximal end), to the distal end 8, exiting the plurality of ports 56 for even distribution in the wound.

Figure 16:
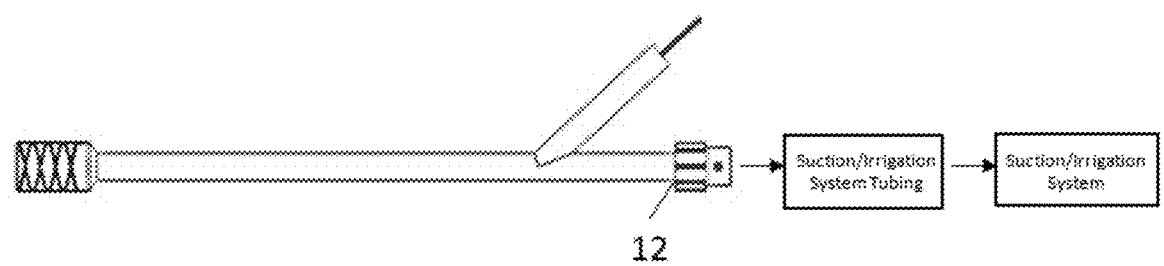
FIG. 16 shows a schematic of an exemplary embodiment of a device for post-operative wound treatment being connected to a suction and/or irrigation device, in accordance with some embodiments.

FIG. 16 is a schematic of a preferred embodiment of the device, as shown in FIGS. 4a and 4b, being used with suction and/or irrigation therapy. The device fitting 12 (as described in FIGS. 4a and 4b) may connect to the suction and/or irrigation therapy system tubing. The suction and/or irrigation therapy may be an NPWT system. The suction therapy may be delivered from a portable or central suction system. The suction and/or irrigation may be provided from any system that is able to provide suction and/or irrigation through an elongate hollow shaft.

Figure 17:
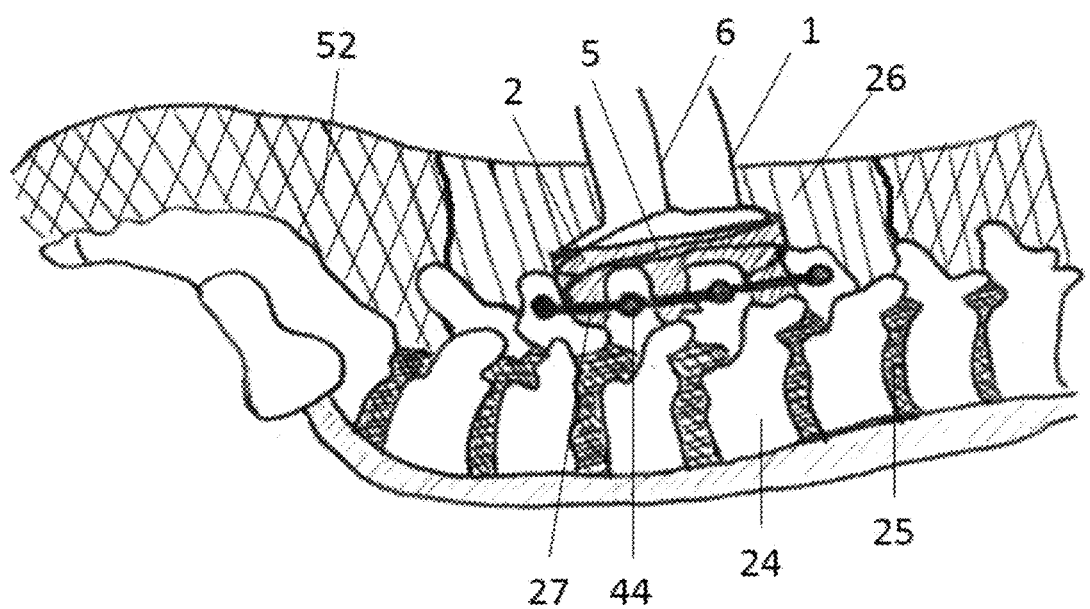
FIG. 17 shows a cross-section view of a device for post-operative wound treatment placed in a spinal wound, in accordance with some embodiments.

FIG. 17 shows a lateral view of the spine with vertebrae 24, disc space 25, and tissue 52. The device from FIGS. 4a and 4b, including an elongate shaft 1, removal element 5 with trailing end 6, and wound dressing 2, is placed in the wound space 26 next to existing instrumentation, including rods 27 and screws 44. This device may be used with a suction and/or irrigation system or any of the other therapies described in this specification.

Figure 18:
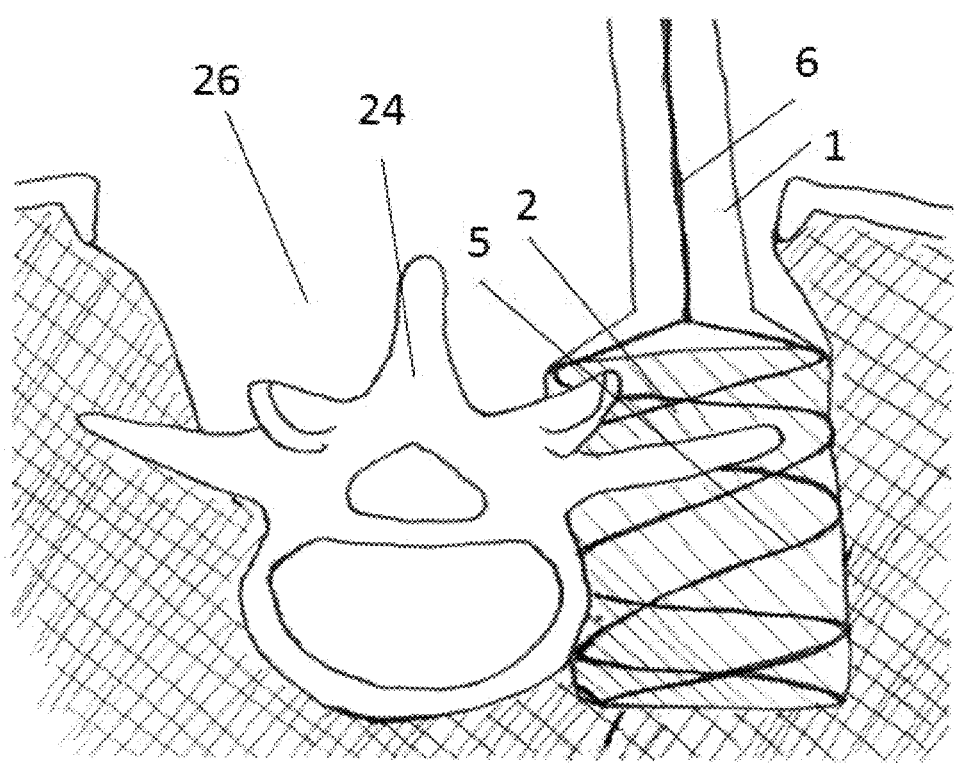
FIG. 18 shows a superior view of a device for post-operative wound treatment placed in a spinal wound, in accordance with some embodiments.

FIG. 18 shows a superior view of the spine with vertebra 24. The device from FIGS. 4a and 4b, including an elongate shaft 1, removal element 5 with trailing end 6, and wound dressing 2, is placed in the wound space 26.

Figure 19:
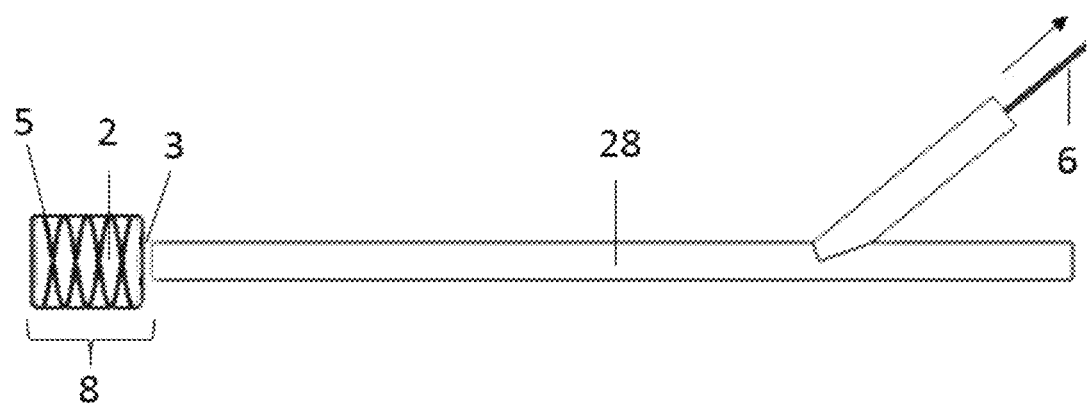
FIG. 19 shows a side view of the removal element being pulled axially, in accordance with some embodiments.

FIGS. 19-22 illustrate a method for device removal. In particular, FIG. 19 shows the trailing end 6 of the removal element 5 being pulled axially (in the direction of the arrow). The trailing end 6 of the removal element 5 spans the length of the lumen of the elongate shaft 28. The distal end 8 of the removal element 5 encompasses the wound dressing 2. The elongate shaft 28 internal end 3 abuts the wound dressing 2. FIG. 19 shows the device as described in FIGS. 4a and 4b.

Figure 20A:
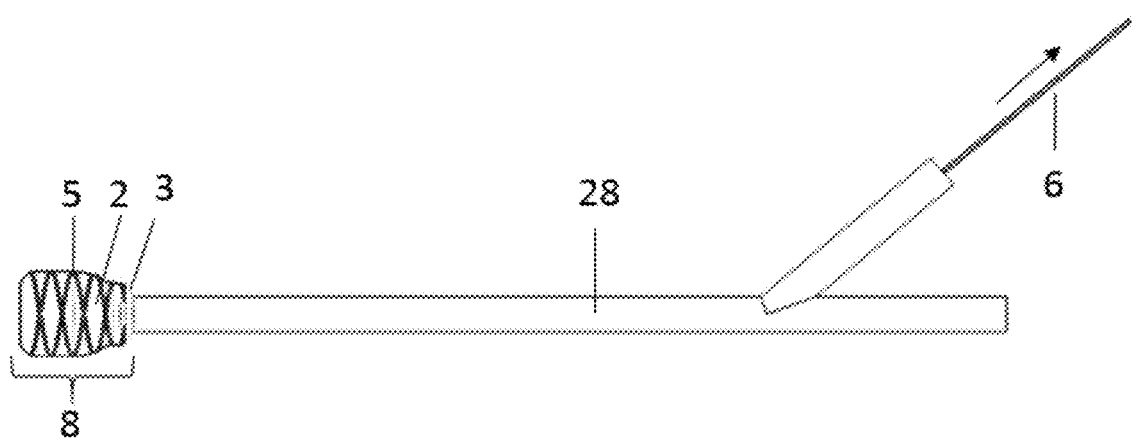
FIG. 20*a* shows a side view of the wound dressing beginning to collapse due to the lengthening and narrowing of the removal element, in accordance with some embodiments.

FIG. 20a shows the distal end 8 of the removal element 5 narrowing, collapsing the wound dressing 2. The trailing end 6 of the removal element 5 spans the length of the lumen of the elongate shaft 28. The distal end 8 of the removal element 5 encompasses the wound dressing 2. The elongate shaft 28 internal end 3 abuts the wound dressing 2. FIG. 20a shows the device as described in FIGS. 4a and 4b.

Figure 20B:
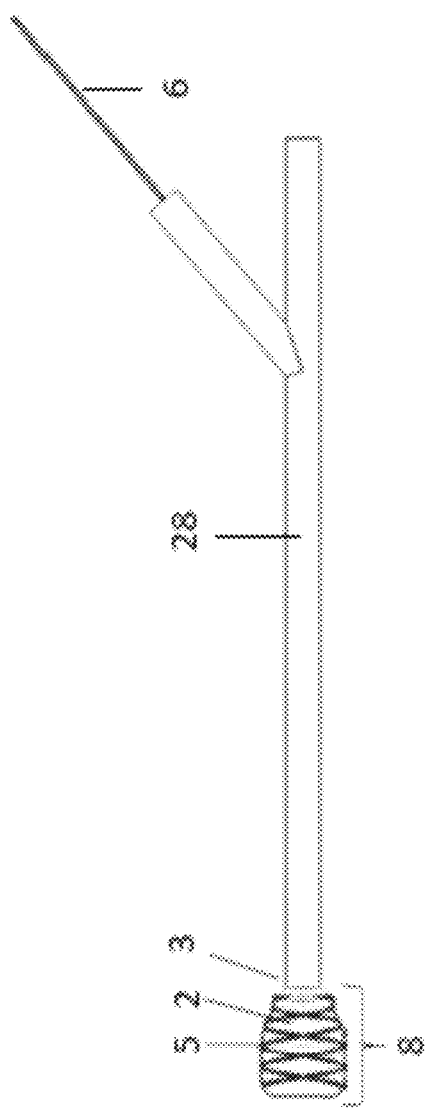
FIG. 20*b* shows a side view of the wound dressing having a sponge partially retracted in an initial position, in accordance with some embodiments.

FIG. 20b shows a device having a partially retracted sponge in an initial position. FIG. 20b shows the device as described in FIGS. 4a and 4b.

Figure 21A:
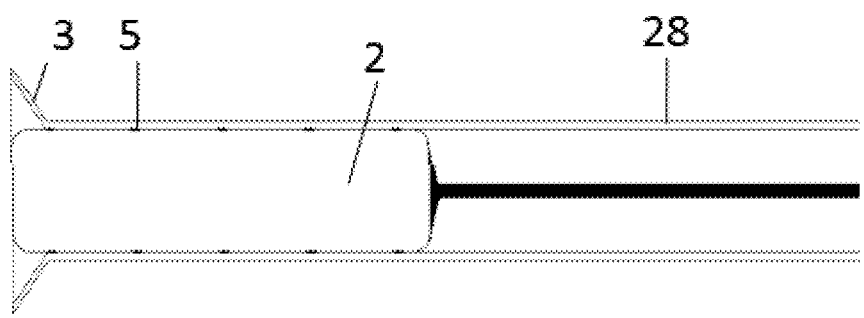
FIG. 21*a* shows a cross-section view of a fully collapsed and retracted wound dressing into the elongate shaft, in accordance with some embodiments.

FIG. 21a shows the fully collapsed removal element 5 and wound dressing 2 after having been collapsed and retracted into the elongate shaft 28, proximally past the internal end 3 having a flare. FIG. 21a shows the device as described in FIGS. 4a and 4b.

Figure 21B:
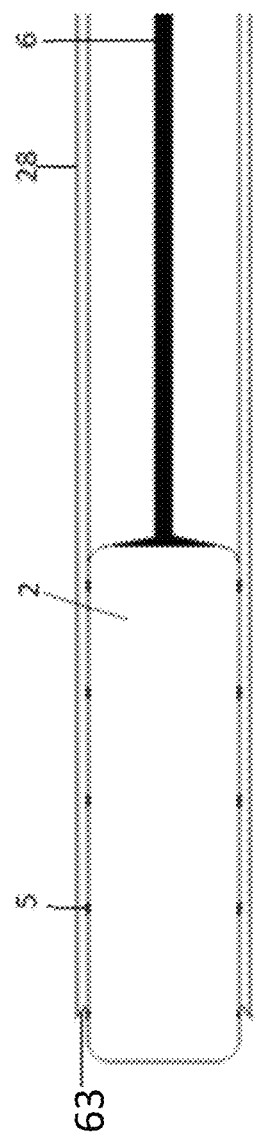
FIG. 21*b* shows a cross-section view of a fully collapsed and retracted wound dressing into the elongate shaft having an internal chamfer, in accordance with some embodiments.

FIG. 21b shows the fully collapsed removal element 5 and wound dressing 2 after having been collapsed and retracted into the elongate shaft 28, proximally past the internal end 3 having an internal chamfer 63. FIG. 21b shows the device as described in FIGS. 4a and 4b.

Figure 22:
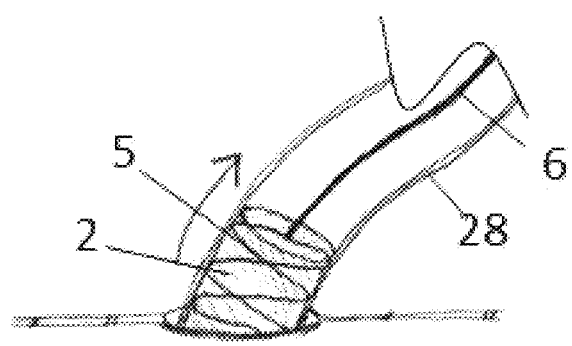
FIG. 22 shows a side view of a device for post-operative wound treatment being removed out of a closed wound, in accordance with some embodiments.

FIG. 22 shows the elongate shaft 28 being removed through the closed wound. The removal element 5 is fully collapsed around the wound dressing 2 and has been retracted into the elongate shaft 28. The trailing end 6 of the biaxial braid spans the length of the lumen of the elongate shaft 28. FIG. 22 shows the device as described in FIGS. 4a and 4b.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A post-operative surgical site wound treatment device comprising:
   an elongate shaft extending along a longitudinal axis, the elongate shaft comprising a distal portion having a distal end that comprises a first inner diameter and the elongate shaft having a second inner diameter at a position proximal to the distal end, wherein the first inner diameter is greater than the second inner diameter and forms a flared internal end; and
   a wound dressing configured to retract into the distal end, wherein the flared internal end is configured to guide the wound dressing into the elongate shaft during retraction of the wound dressing;
   wherein the device is configured to be coupled to an external system that provides any one of suction, delivery of an irrigating fluid, delivery of an antibiotic, or a combination thereof, to the wound through a first lumen of the elongate shaft.

2. The device of claim 1, wherein the external system comprises a negative pressure wound therapy (NPWT) device.

3. The device of claim 1, wherein the wound dressing is a sterile, open cell reticulated, hydrophobic, polyurethane foam.

4. The device of claim 1, comprising a removal element coupled to the wound dressing, the removal element comprising a trailing end that spans a length of the elongate shaft, the removal element being collapsible.

5. The device of claim 4, wherein the removal element has an expanded distal end with a diameter or width greater than the second inner diameter of the elongate shaft.

6. The device of claim 4, wherein the removal element is collapsible to a diameter or width less than the second inner diameter of the elongate shall.

7. The device of claim 4, wherein the removal element is woven into the wound dressing, around the wound dressing, or a combination thereof, wherein the removal element collapses the wound dressing when the trailing end is pulled axially.

8. The device of claim 7, wherein the removal element comprises a helical braid.

9. The device of claim 4, wherein the removal element comprises a plurality of hollow structures.

10. The device of claim 9, wherein the hollow structures comprises a plurality of fluid ports configured for fluid diffusion.

11. The device of claim 9, wherein the plurality of fluid ports is configured to receive an antibiotic via the trailing end and distribute the antibiotic in the wound.

12. The device of claim 1, wherein the elongate shaft comprises a y-split forming a first external arm and a second external arm at a proximal portion of the elongate shaft.

13. The device of claim 12, wherein the first external arm of the elongate shaft is configured to couple to the external system.

14. The device of claim 12, wherein the first external arm is configured to provide suction to the wound through the first lumen, and the second external arm of the elongate shaft is configured to deliver the irrigating fluid, the antibiotic, or combinations thereof to the wound through the first lumen of the elongate shaft.

15. The device of claim 1, wherein the elongate shaft comprises a second lumen.

16. The device of claim 15, wherein the first lumen is configured to provide suction to the wound, wherein the second lumen is configured to deliver the irrigating fluid, the antibiotic, or combinations thereof to the wound.

17. The device of claim 1, comprising tubing forming a hollow extension distal to the distal end and into the wound dressing, wherein the hollow extension comprises an extension of the first lumen, of a second lumen, or both.

18. The device of claim 17, wherein the hollow extension comprises a plurality of holes disposed circumferentially, axially, or any combination thereof, wherein the plurality of holes are disposed on the portion of the tubing located within the wound dressing.

19. The device of claim 18, wherein each hole of the plurality of holes has a diameter of about 0.2 mm to about 0.8 mm.

20. The device of claim 17, wherein the tubing comprises a closed tip.

* * * * *